US006844154B2

(12) United States Patent
Landers

(10) Patent No.: US 6,844,154 B2
(45) Date of Patent: Jan. 18, 2005

(54) HIGH THROUGHPUT METHODS FOR HAPLOTYPING

(75) Inventor: John E. Landers, Marlboro, MA (US)

(73) Assignee: PolyGenyx, Inc., Worchester, MA (US)

( * ) Notice: Subject to any disclaimer, the term of this patent is extended or adjusted under 35 U.S.C. 154(b) by 0 days.

(21) Appl. No.: 09/823,257

(22) Filed: Mar. 30, 2001

(65) Prior Publication Data

US 2003/0096231 A1 May 22, 2003

Related U.S. Application Data

(60) Provisional application No. 60/194,425, filed on Apr. 4, 2000.

(51) Int. Cl.[7] ............................. C07H 21/04; C12Q 1/68
(52) U.S. Cl. ......................... 435/6; 435/91.1; 435/91.2; 536/23.1
(58) Field of Search .......................... 435/91.2, 6, 91.1; 536/23.1

(56) References Cited

U.S. PATENT DOCUMENTS

| | | | |
|---|---|---|---|
| 5,525,494 A | * | 6/1996 | Newton ...................... 435/91.2 |
| 5,578,458 A | | 11/1996 | Caskey et al. |
| 5,612,179 A | | 3/1997 | Simons |
| 5,654,148 A | | 8/1997 | Lebo |
| 5,665,572 A | | 9/1997 | Ikeda et al. |
| 5,747,251 A | | 5/1998 | Carson et al. |
| 5,750,352 A | | 5/1998 | Vogelstein et al. |
| 5,763,167 A | | 6/1998 | Conrad |
| 5,763,181 A | | 6/1998 | Han et al. |
| 5,789,168 A | | 8/1998 | Leushner et al. |
| 5,789,568 A | | 8/1998 | Simons |
| 5,851,762 A | | 12/1998 | Simons |
| 5,858,659 A | * | 1/1999 | Sapolsky et al. ............... 435/6 |
| 5,866,336 A | | 2/1999 | Nazarenko et al. |
| 5,911,952 A | | 6/1999 | Tsuji |
| 5,972,604 A | | 10/1999 | Santamaria et al. |
| 5,989,823 A | | 11/1999 | Jayasena et al. |
| 5,998,146 A | | 12/1999 | Latva et al. |
| 5,998,204 A | | 12/1999 | Tsien et al. |
| 6,008,378 A | | 12/1999 | Tsien et al. |
| 6,015,675 A | | 1/2000 | Caskey et al. |
| 6,153,379 A | * | 11/2000 | Caskey et al. .................. 435/6 |
| 6,210,878 B1 | * | 4/2001 | Pinkel et al. ................... 435/6 |
| 6,306,643 B1 | * | 10/2001 | Gentalen et al. .......... 435/287.2 |
| 6,327,410 B1 | * | 12/2001 | Walt et al. ................... 385/115 |
| 6,410,231 B1 | * | 6/2002 | Arnold et al. .................. 435/6 |
| 2001/0031467 A1 | | 10/2001 | Dapprich |

FOREIGN PATENT DOCUMENTS

| | | |
|---|---|---|
| EP | 0 967 291 A1 | 12/1999 |
| WO | WO 93/09249 A1 | 5/1993 |
| WO | WO 99/04038 A2 | 1/1999 |
| WO | WO 99/06598 A1 | 2/1999 |
| WO | WO 99/57308 A1 | 11/1999 |
| WO | WO 99/64590 A1 | 12/1999 |
| WO | WO 00/11223 A1 | 3/2000 |
| WO | WO 01/42510 A2 | 6/2001 |

OTHER PUBLICATIONS

Cronin et al. "Cystic fibrosis mutation detection by hybridization to light–generated DNA probe arrays" Human Mutation, vol. 7, pp. 244–255, 1996.*

Gentalen, E., et al., "A novel method for determining linkage between DNA sequences: hybridization to paired probe arrays," Nucleic Acids Research, 1999, vol. 27, No. 6, pp. 1485–1491.

International Search Report of PCT/US01/10173, published as WO 01/75163, dated Jul. 5, 2002.

Berg, E.S. et al., "Use of DNA amplification (PCR) and direct DNA sequencing in the characterization of C4 alleles", Ann. Hum. Genet., Jul. 1990, pp. 183–189, vol. 54, Pt. 3.

Bottema, C.D. et al., "Polymerase Chain Reaction Amplification of Specific Alleles: A General Method of Detection of Mutations, Polymorphisms, and Haplotypes", Methods in Enzymology, 1993, pp. 388–402, vol. 218, Academic Press, Inc.

Fanning, G.C. et al., "Polymerase chain reaction haplotyping using 3' mismatches in the forward and reverse primers: application to the biallelic polymorphisms of tumor necrosis factor and lymphotoxin α", Tissue Antigens, Jul. 1997, pp. 23–31, vol. 50, No. 1, Munksgaard, Denmark.

Kaneoka, H. et al., "Solid–Phase Direct DNA Sequencing of Allele–Specific Polymerase Chain Reaction–Amplified HLA–DR Genes", BioTechniques, Jan. 1991, pp. 30, 32, 34, vol. 10, No. 1.

Maeda, M. et al., "A simple and rapid method for HLA–DQA1 genotyping by digestion of PCR–amplified DNA with allele specific restriction endonucleases", Tissues Antigens, 1989, pp. 290–298, vol. 34.

Michalatos–Beloin, S. et al., "Molecular haplotyping of genetic markers 10 kb apart by allele–specific long–range PCR", Nucleic Acids Research, 1996, pp. 4841–4843, vol. 24, No. 23, Oxford University Press.

Mullighan, C.G. et al., "Rapid haplotyping of mutations in the Duffy gene using the polymerase chain reaction and sequence–specific primers", Tissue Antigens, 1998, pp. 195–199, vol. 51, Munksgaard, Denmark.

Peltekova, V.D. et al., "Direct Haplotyping at the Vitamin D, Receptor Locus Improves Genetic Resolution", Journal of Bone and Mineral Research, 1997, pp. 494–495, vol. 12, No. 3, Blackwell Science, Inc., American Society of Bone and Mineral Research.

Petersdorf, E.W. et al., "Analysis of HLA–B* 44 alleles encoded on extended HLA haplotypes by direct automated sequencing", Tissue Antigens, 1994, pp. 211–216, vol. 44, Munksgaard, Denmark.

(List continued on next page.)

Primary Examiner—Jeanine Goldberg
(74) Attorney, Agent, or Firm—Wolf, Greenfield & Sacks, P.C.

(57) ABSTRACT

The invention relates to high throughput methods for determining haplotypes. The high throughput methods are based on hybridization, fluorescence detection, primer extension, MALDI TOF, and HPLC.

23 Claims, 7 Drawing Sheets

OTHER PUBLICATIONS

Petersdorf, E.W. et al., "A comprehensive approach for typing the alleles of the HLA–B locus by automated sequencing", *Tissue Antigens*, Aug. 1995, pp. 73–85, vol. 46, No. 2, Munksgaard, Denmark.

Ruano, G. et al., "Haplotype of multiple polymorphisms resolved by enzymatic amplification of single DNA molecules", *Proc. Natl. Acad. Sci. USA*, Aug. 1990, pp. 6296–6300, vol. 87.

Sarkar, G. et al., "Haplotyping by Double PCR Amplification of Specific Alleles", *BioTechniques*, Apr. 1991, pp. 436, 438, 440, vol. 10, No. 4.

Sommer, S.S. et al., "PCR Amplification of Specific Alleles (PASA) is a General Method for Rapidly Detecting Known Single–Base Changes", *BioTechniques*, Jan. 1992, pp. 82–87, vol. 12, No. 1.

Suzuki, Y. et al., "Allele–Specific Polymerase Chain Reaction: A Method for Amplification and Sequence Determination of a Single Component among a Mixture of Sequence Variants", *Analytical Biochemistry*, 1991, pp. 82–84, vol. 192, Academic Press, Inc.

* cited by examiner

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic Human Oligonucleotide

<400> SEQUENCE: 1
cctcagtgac atccttgcct                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Human Oligonucleotide

<400> SEQUENCE: 2
catgcccatt cttctctggt                                                      20

<210> SEQ ID NO 3
<211> LENGTH: 31
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 3
tttttttttt ttttagtct cccctttccc t                                          31

<210> SEQ ID NO 4
<211> LENGTH: 32
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 4
tttttttttt ttttagtct cccactttcc ct                                         32

<210> SEQ ID NO 5
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 5
agggtggtgc cagaggt                                                         17

<210> SEQ ID NO 6
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 6
agggtggtac cagaggt                                                         17

<210> SEQ ID NO 7
<211> LENGTH: 20
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: phosphate group attached

<400> SEQUENCE: 7
acttgacagc gagtgtgctg                                                      20

<210> SEQ ID NO 8
<211> LENGTH: 18
<212> TYPE: DNA
<213> ORGANISM: Artificial Sequence

```
<220> FEATURE:
<223> OTHER INFORMATION: Synthetic Human Oligonucleotide

<400> SEQUENCE: 8 gtcccttttgc tgcgtgac                                              18

<210> SEQ ID NO 9
<211> LENGTH: 40
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 9
tttttttttt tttttttttt tttcacccaa tggaagccat                       40

<210> SEQ ID NO 10
<211> LENGTH: 40
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 10
tttttttttt tttttttttt tttcacccaa tagaagccat                       40

<210> SEQ ID NO 11
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 11
aggaaatcgg cagctgt                                                17

<210> SEQ ID NO 12
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 12
aggaaatcag cagctgt                                                17

<210> SEQ ID NO 13
<211> LENGTH: 17
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(3)
<223> OTHER INFORMATION: Biotin attached

<400> SEQUENCE: 13
aggaaatcgg cagctgt                                                17

<210> SEQ ID NO 14
<211> LENGTH: 17
```

```
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(3)
<223> OTHER INFORMATION: Biotin attached

<400> SEQUENCE: 14
aggaaatcag cagctgt                                                        17

<210> SEQ ID NO 15
<211> LENGTH: 24
<212> TYPE: DNA
<213> ORGANISM: Artificial Sequence
<220> FEATURE:
<223> OTHER INFORMATION: Synthetic Human Oligonucleotide

<400> SEQUENCE: 15
gaacagcaat gcacattacc atgg                                                24

<210> SEQ ID NO 16
<211> LENGTH: 25
<212> TYPE: DNA
<213> ORGANISM: Artificial Sequence
<220> FEATURE:
<223> OTHER INFORMATION: Synthetic Human Oligonucleotide

<400> SEQUENCE: 16
ctgtcaagta tttctccgca gcata                                               25

<210> SEQ ID NO 17
<211> LENGTH: 40
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 17
tttttttttt tttttttttt tttgccacaa tgaatgacat                               40

<210> SEQ ID NO 18
<211> LENGTH: 40
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(1)
<223> OTHER INFORMATION: amino group attached

<400> SEQUENCE: 18
tttttttttt tttttttttt tttgccacaa tcaatgacat                               40

<210> SEQ ID NO 19
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 19
atgtcattga ttgtggc                                                        17
```

```
<210> SEQ ID NO 20
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 20
atgtcattca ttgtggc                                                17

<210> SEQ ID NO 21
<211> LENGTH: 17
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(3)
<223> OTHER INFORMATION: biotin attached

<400> SEQUENCE: 21
tgtataatca gaattat                                                17

<210> SEQ ID NO 22
<211> LENGTH: 17
<212> TYPE: DNA
<213> ORGANISM: Artificial Sequence
<220> FEATURE:
<223> OTHER INFORMATION: Synthetic Human Oligonucleotide
<221> NAME/KEY: misc_feature
<222> LOCATION: (1)..(3)
<223> OTHER INFORMATION: Biotin attached

<400> SEQUENCE: 22
tgtataatta gaattat                                                17

<210> SEQ ID NO 23
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 23
tgtataatca gaattat                                                17

<210> SEQ ID NO 24
<211> LENGTH: 17
<212> TYPE: DNA
<213> ORGANISM: Artificial Sequence
<220> FEATURE:
<223> OTHER INFORMATION: Synthetic Human Oligonucleotide

<400> SEQUENCE: 24
tgtataatta gaattat                                                17
```

HIGH THROUGHPUT METHODS FOR HAPLOTYPING

RELATED APPLICATIONS

This application claims priority under 35 U.S.C. §119 to U.S. Provisional Patent Application No. 60/194,425, filed on Apr. 4, 2000, the entire contents of which is hereby incorporated by reference.

FIELD OF THE INVENTION

The invention relates to high throughput methods for single nucleotide polymorphism (SNP) haplotyping. In particular, the methods involve analysis of polymorphic loci of a nucleic acid using techniques involving hybridization, primer extension, MALDI TOF, HPLC, and/or fluorescence detection.

BACKGROUND OF THE INVENTION

In recent years, genetic alterations which cause or contribute to many different diseases have been identified. A few of the diseases associated with genetic alterations are genetically simple and are associated with a single genetic alteration. Once the genetic alteration associated with a genetically simple disease is identified, characterization and diagnosis of the disease is relatively simple. Most phenotypic traits and diseases, however, are genetically complex. The genetic complexity can arise as a result of the interaction or disruption of multiple genes, incomplete penetrance, genetic heterogeneity, and/or environmental/random causes (phenocopy). (Lander, E. S. and Schork, N. J., *Science*, 265:2037–2048 (1994)). Mapping of complex traits or diseases requires that the entire genome be scanned in order to identify all genomic regions that potentially contribute to the development of that trait or disease. In general, genome wide scans are performed using polymorphic DNA markers to determine which markers segregate with a complex trait of interest. The loci which are identified as contributing to a disease can then be mapped to specific genomic regions based on the known chromosomal locations of the markers segregating with or "linked" to that trait.

Several types of DNA polymorphisms or markers occur in the human genome and can be used in genome wide scans. These include restriction fragment length polymorphisms (RFLPs), microsatellites or simple sequence length polymorphisms (SSLPs), and single nucleotide polymorphisms (SNPs).

RFLPs are single nucleotide changes (point changes or insertion/deletion changes) which alter a restriction site and thus the digestion pattern of a given segment of DNA. RFLPs were the first type of polymorphism identified and were used as a tool to construct early genetic linkage maps in humans. RFLPs are unsuitable for a large scale analysis of populations, however, because they are unreliable and not amenable to automation. RFLPs are unreliable when used to analyze genetically-related individuals, because RFLPs have only two alleles, one with the restriction site and one without and related individuals generally have the same allele on both chromosomes. Additionally, RFLPs are not amenable to automation because RFLP detection requires the use of Southern Blot techniques which are not easily automated.

Microsatellite markers or SSLPs are sequences that are repeated in tandem, with the number of repeats resulting in multiple alleles of different lengths. Microsatellite markers are useful for identifying genes involved in traits which follow simple Mendelian, monogenic patterns of inheritance. Microsatellites, however, have proven to be unsuitable for studies involving traits which follow non-Mendelian complex patterns of inheritance because microsatellites are not optimally abundant, occurring only once every few kilobases. Microsatellites also have a high mutation and recombination rate which makes them genetically unstable. Microsatellite markers are not amenable to high throughput analysis because they can only be analyzed using PCR and gel-based assays, which require a substantial investment in labor and time as well as cost.

SNPs are single base pair positions in the genome at which different sequence alternatives (alleles) exist in the population at frequencies of greater than 1%. SNPs are extremely stable and dense within the genome, but are not optimally informative because they only identify a single loci, and thus have low statistical power.

SUMMARY OF THE INVENTION

The invention relates to a high throughput method for SNP-based haplotyping, which is capable of assessing multiple alleles in large numbers of genomic samples. SNP haplotype analysis is much more informative than single SNP loci analysis because it enables the analysis of complex traits. Each haplotype segregates as a contiguous set of alleles within families and consideration of multiple closely-linked marker loci can provide a larger number of alleles, each of low frequency. If a chromosomal region has multiple polymorphic loci, none of which are individually very informative, then haplotypes of these loci can be used to define a new locus with a heterozygosity and informativeness significantly beyond that of any single marker contained therein. The high throughput method of SNP-haplotyping described and claimed herein provides improved methods for SNP-haplotyping that can dramatically increase the rate of haplotype analysis and enable large scale haplotyping studies.

In one aspect the invention is a method for haplotyping. The method involves analyzing a first polymorphic locus of a nucleic acid within a sample by specifically capturing the nucleic acid on a surface wherein the step of capturing the nucleic acid on the surface identifies a first allele of a first SNP of the polymorphic locus, repeating the analysis of the first polymorphic locus of the nucleic acid to identify a second allele of the first SNP of the polymorphic locus, separately analyzing a second SNP of a polymorphic locus of the nucleic acid sample to identify both alleles of the second SNP, and determining the haplotype based on the identification of each allele of each SNP. The term "separately" refers to analysis in discreet physical locations. Although the first and second SNPs are analyzed separately, they may be analyzed simultaneously. The different SNP alleles may also be analyzed on the same surface (i.e. surface of a slide) as long as they are analyzed on different spots or discreet locations of the slide from one another.

In some embodiments the second SNP is analyzed using a method selected from the group consisting of hybridization, primer extension, MALDI TOF, and HPLC. In one preferred method the second SNP is analyzed by hybridization of the nucleic acid sample with an ASO complementary to a first allele of the second SNP and an ASO complementary to a second allele of the second SNP.

In other embodiments the nucleic acid is captured by hybridization with an ASO, and wherein the ASO is fixed to a surface. Preferably a first ASO complementary to a first allele of the first SNP and a second ASO complementary to a second allele of the first SNP are hybridized to the surface and are used to capture the nucleic acid.

In some embodiments each ASO corresponding to an allele of the first SNP further includes a spacer sequence. Preferably the spacer sequence is selected from the group consisting of a poly-T, poly-A, poly-C, and poly-G.

In this embodiment each of the ASOs corresponding to an allele of the second SNP may be hybridized independently to the nucleic acid sample. Alternatively the alleles of the second SNP are analyzed simultaneously with one another.

In preferred embodiments at least one of the ASOs complementary to an allele of the first SNP and at least one of the ASOs complementary to an allele of the second SNP contains a fluorescent label or quencher, the fluorescent label or quencher of the two ASOs, being distinct from one another.

The surface may be any type of solid support, such as, for instance, a multiwell dish, a chip, a slide or a bead.

The nucleic acid sample may be prepared by any method known in the art. For instance the nucleic acid may be prepared by PCR amplification of a polymorphic locus from a genomic DNA sample. Alternatively, the nucleic acid sample may be a reduced complexity genome. In some embodiments the nucleic acid sample is labeled with a first label.

According to other embodiments the presence of one set of alleles at the polymorphic locus is associated with a disease and the haplotyping method is performed to identify predisposition to the disease.

The methods for haplotyping may also involve analysis of more than two SNPs. In one embodiment a third SNP of a polymorphic locus of the nucleic acid sample is analyzed to identify both alleles of the third SNP, and the haplotype is determine based on the identification of each allele of each SNP. In another embodiment a fourth SNP of a polymorphic locus of the nucleic acid sample is analyzed to identify both alleles of the fourth SNP, and the haplotype is determine based on the identification of each allele of each SNP. Many genes are known to have multiple SNPs, for example the APOE gene has a reported 23 variable sites. Therefore the haplotyping technology of the invention involves the analysis of haplotypes containing multiple (i.e. >2) SNPs, e.g., using a microarray-based haplotyping method that can determine the haplotype for any number of SNPs with just two hybridizations.

The invention in other aspects relates to a method for haplotyping by analyzing a genotype of a first SNP of a polymorphic locus of a nucleic acid within a sample in solution by detecting the presence or absence of a first labeled probe which specifically identifies a first putative allele of the SNP and detecting the presence or absence of a second labeled probe which specifically identifies a second putative allele of the SNP, separating the nucleic acid sample based on the genotype of the first SNP, and analyzing a second SNP of the polymorphic locus of the separated nucleic acid samples to identify the haplotype of the nucleic acid.

In preferred embodiments the analysis of the first SNP is performed using fluorescence detection and the nucleic acid sample is separated using flow cytometry.

In other embodiments the second SNP is analyzed using a method selected from the group consisting of hybridization, primer extension, MALDI TOF, and HPLC.

According to another aspect of the invention a method for haplotyping is provided. The method involves labeling first and second SNPs of a polymorphic locus of a nucleic acid within a sample in solution with a first, second, third, and fourth labeled probe which specifically identifies a first and second putative allele of the first SNP and a first and second putative allele of the second SNP respectively, separating the labeled nucleic acid sample into single nucleic acid molecules, detecting the presence or absence of the first, second, third, and fourth labeled probes on the single nucleic acid molecules to identify the haplotype of the nucleic acid.

In one embodiment the probes are labeled with fluorescence molecules and optionally each of the fluorescent molecules of the labeled probes is spectrally distinct.

The invention in another aspect is a method for haplotyping by performing four hybridization reactions on a nucleic acid sample, each of the four hybridization reactions involving one labeled probe specific for one allele of one of two SNPs, each of the labeled probes labeled with a spectrally distinct label and wherein each label on the probe specific for a first of the two SNPs is a spectral pair with the label on each probe specific for the second of the two SNPs, bringing each of the labeled probes in each hybridization reaction within energy transfer distance from one another, exciting one of the labeled probes in each hybridization reaction, and detecting electromagnetic radiation released from the other labeled probe as a signal, wherein the presence or absence of a signal for each hybridization reaction is an indicator of the haplotype of the nucleic acid sample. The method can be performed in solution or on a surface.

In some embodiments each hybridization reaction is performed in a separate vessel. In other embodiments the labeled probes are brought within energy transfer proximity of one another using binding partners, such as avidin and biotin. In yet other embodiments the labeled probes are labeled ASOs.

A kit is provided according to other aspects of the invention. The kit includes one or more containers housing: a first set of ASOs, wherein the first set of ASOs represents two ASOs, each containing one of the two alleles of a first SNP in a polymorphic locus, a second set of ASOs, wherein the second set of ASOs represents two ASOs, each containing one of the two alleles of a second SNP in the polymorphic locus, and instructions for performing a hybridization reaction to determine a haplotype from a genomic DNA sample using the first and second sets of ASOs.

Optionally the kit may include a set of PCR primers for amplifying the polymorphic locus of the genomic DNA sample.

In some embodiments the first set of ASOs are fixed to a surface and the second set of ASOs are labeled.

In other embodiments the ASOs include a spacer and the spacer sequence is selected from the group consisting of a poly-T, poly-A, poly-C, and poly-G.

Each of the limitations of the invention can encompass various embodiments of the invention. It is, therefore, anticipated that each of the limitations of the invention involving any one element or combination of elements, can be included in each aspect of the invention.

BRIEF DESCRIPTION OF THE SEQUENCES

Figure 1:
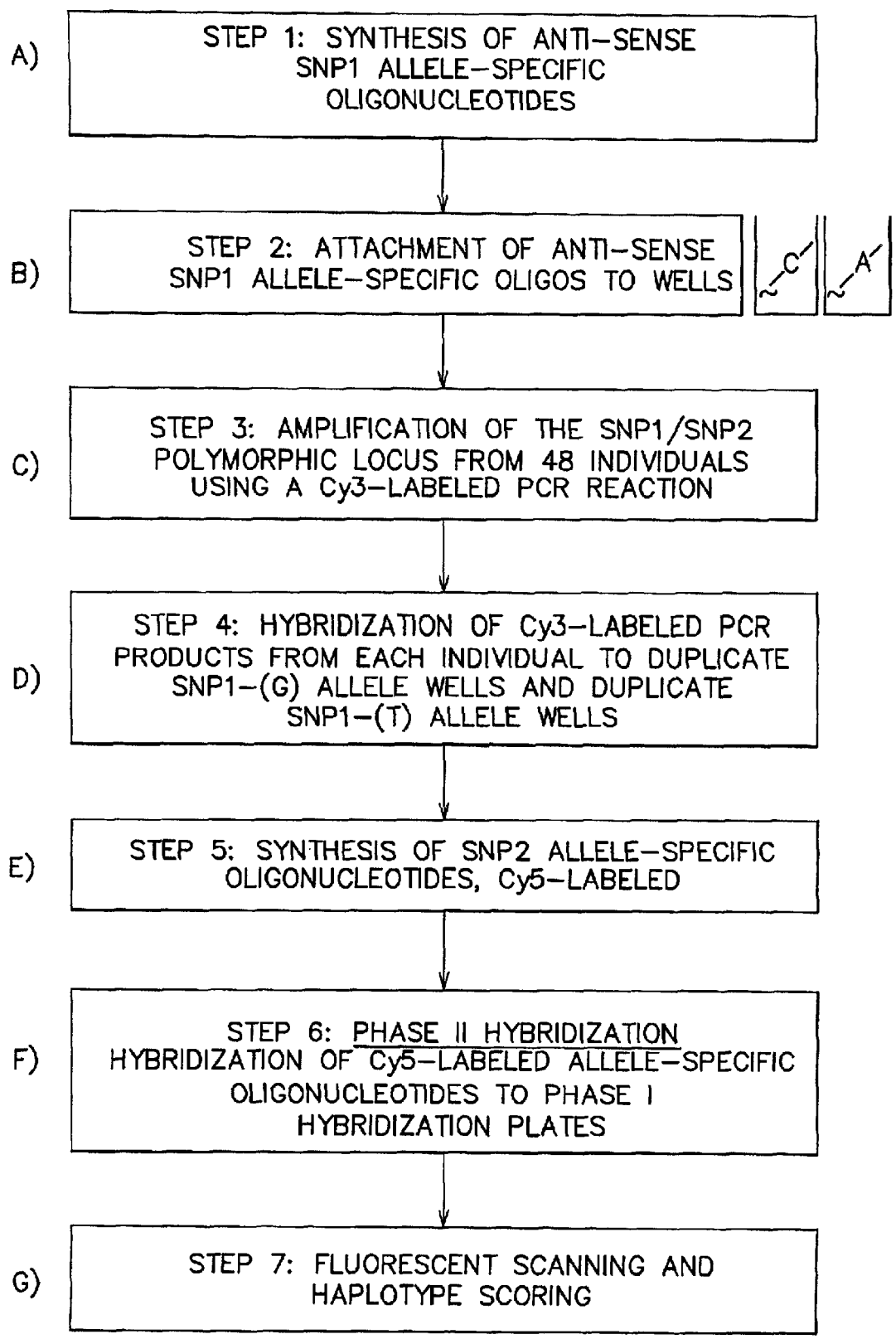
FIG. 1 is a flow chart and diagram depicting an exemplary method for performing high throughput SNP haplotyping analysis.

SEQ ID NO. 1 is a PCR primer for M13$^{(For)}$—CCTCAGTGACATCCTTGCCT.

SEQ ID NO. 2 is a PCR primer for M13$^{(Rev)}$ CATGCCCATTCTTCTCTGGT.

SEQ ID NO. 3 is a SNP1-(G detecting) oligo: NH$_2$-(T)$_{15}$AGTCTCCC(C)TTTCCCT.

SEQ ID NO. 4 is SNP1-(T detecting) oligo: NH$_2$-(T)$_{15}$AGTCTCCC(A)CTTTCCCT.

SEQ ID NO. 5 is SNP2-(C detecting) oligo: AGGGTGGT(G)CCAGAGGT.

SEQ ID NO. 6 is SNP2-(T-detecting) oligo: AGGGTGGT(A)CCAGAGGT.

SEQ ID NO:7 is a PCR forward primer: [PO4]-ACTTGACAGCGAGTGTGCTG.

SEQ ID NO:8 is a PCR reverse primer: GTCCCTTTGCTGCGTGAC.

SEQ ID NO:9 is a BAR-G oligo: NH$_2$-(T)$_{23}$CACCCAATGGAAGCCAT.

SEQ ID NO:10 is a BAR-A oligo: NH$_2$-(T)$_{23}$CACCCAATAGAAGCCAT.

SEQ ID NO:11 is a BARPIIGcc oligo: AGGAAATCGGCAGCTGT.

SEQ ID NO:12 is a BARPIIAcc oligo: AGGAAATCAGCAGCTGT.

SEQ ID NO:13 is a biotinylated BAR-PIIG oligo: [Bio]-AGGAAATCGGCAGCTGT.

SEQ ID NO:14 is a biotinylated BAR-PIIA oligo: [Bio]-AGGAAATCGGCAGCTGT.

SEQ ID NO:15 is a PCR forward primer: GAACAGCAAT-GCACATTACCATGG.

SEQ ID NO:16 is a PCR reverse primer: CTGTCAAG-TATTTCTCCGCAGCATA.

SEQ ID NO:17 is an amine-labeled 4035AmC oligo: NH$_2$(T)$_{23}$GCCACAATGAATGACAT.

SEQ ID NO:18 is an amine-labeled 4035AmC oligo: NH$_2$(T)$_{23}$GCCACAATCAATGACAT.

SEQ ID NO:19 is a 4035ColdCompG oligo: ATGTCAT-TGATTGTGGC.

SEQ ID NO:20 is a 4035ColdCompC oligo: ATGTCAT-TCATTGTGGC.

SEQ ID NO:21 is a biotinylated 4035-CB oligo: Biotin-TGTATAATCAGAATTAT.

SEQ ID NO:22 is a biotinylated 4035-TB oligo: Biotin-TGTATAATTAGAATTAT.

SEQ ID NO:23 is a cold competitive 4035-C oligo: TGTATAATCAGAATTAT.

SEQ ID NO:24 is a cold competitive 4035-T oligo: TGTATAATTAGAATTAT.

DETAILED DESCRIPTION

In recent years, certain diseases have been identified where the occurrence of certain polymorphic haplotypes are associated with either an increase in susceptibility for developing disease or with differences in the onset progression and/or severity of the disease. These diseases include, for example, multiple sclerosis (Kalman, B. and Lublin, F. D., *Biomed and Pharmacother.*, 53:358–370 (1999)), insulin-dependent diabetes mellitus (Deschammps, I. and Khalil, I, *Diabetes Metabol. Rev.*, 9.71–92 (1993)), and narcolepsy (Billiard, M. and Seignaled, J., *Lancet*, 1:226–227 (1985)). The haplotypes associated with these disease susceptibility loci have been identified using standard technology, such as RFLP or microsatellite analysis. Alzheimer's Disease is one of the few diseases where the predisposing haplotype is composed of commonly inherited SNPs (Corder, E. H., et al., *Science*, 261:921–923 (1993)). These SNPs occur in the epsilon allele of the apolipoprotein E locus (APOE). In Alzheimer's Disease, approximately half of late-onset familial and sporadic Alzheimer's Disease (i.e., development of disease by the age of 70 years) is associated with inheriting the e4/e4 SNP haplotype. Individuals inheriting any other combination of the e2, e3, or e4 alleles have a significantly reduced risk of developing late-onset Alzheimer's Disease, with the lowest risk for Alzheimer's Disease being associated with the e2/e3 haplotype. Additionally, the precise haplotype an individual inherits can also predict the age of onset of disease from younger than 70 years for the e4/e4 haplotype to greater than 90 years for the e2/e3 haplotype, a more than 20 year shift in susceptibility.

The invention involves the identification of high throughput methods for screening DNA to identify polymorphic haplotypes and to enable identification of haplotypes associated with predisposition to these and other diseases as well as other genetically associated traits. The high throughput method is based on the analysis of SNPs. In one aspect the invention involves the use of a capture step to analyze the SNPs.

Two types of SNP haplotyping methods have been described in the prior art, the 3' mismatch PCR-SSP and SMD methods. 3' mismatch PCR-sequence-specific primers (PCR-SSP) or allele-specific amplification (ASA) is a PCR-based method which utilizes a primer pair such that the 3' base on each primer represents one of the SNPs within a SNP1/SNP2 haplotype. The primers are mixed with the nucleic acid sample and allowed to anneal each to its respective SNP within the nucleic acid sample and PCR is performed. If the nucleic acid sample contains both SNP1 and SNP2, a PCR product will be produced and detected in a gel or hybridization method. If the nucleic acid sample does not contain either or both SNP1 or SNP2, then no PCR product will be produced. By mixing different sets of 3' mismatch primers, one can determine the haplotype of the SNPs in the targeted genomic region by determining which primer set results in a PCR product. One of the disadvantages of this method is that it requires extensive methodology including optimization of PCR conditions for every primer pair utilized and electrophoretic analysis. These methods are not conducive to high throughput analysis of haplotypes.

Single molecule dilution (SMD) is a method which involves serial dilution of genomic DNA until an average of one molecule or haploid equivalent of DNA per 5–10 aliquots is reached. After dilution, a multi-step PCR reaction known as a booster PCR is performed with each of the 5–10 aliquots. The PCR reactions are analyzed by gel electrophoresis and then with dot blot hybridization or direct sequencing to determine haplotypes. There are many disadvantages associated with this technique, including the many laborious steps which prevent high throughput screening, the increased likelihood of shearing due to the dilution steps, and sensitivity of the reaction to any DNA contamination.

In order for a marker to be effective in genetically dissecting complex traits in genome wide scans, the marker should be abundant, stable, informative, amenable to high throughput analysis, have high scoring power, and be useful in linkage disequilibrium analysis. The ability for a marker to be amenable to high throughput analysis is very important. Due to the genetic complexity with which most phenotypic traits and diseases arise, genome wide scan analysis requires the genotyping of thousands of individuals in order to achieve adequate statistical power. The polymorphic markers used, thus, must be amenable to a high throughput and cost efficient method of analysis in order to analyze the extremely large numbers of samples required. The SNP-based methods of the invention are high throughput, whereas the 3' mismatch PCR-SSP and SMD methods are not.

Scoring power is also important. Scoring power refers to the degree of ease, accuracy and reliability with which a marker's presence or absence can be determined in the genome that is being analyzed. In order to genotype thousands of test genomes in a time and cost efficient manner, the polymorphic marker must be easily scored as either present or absent and this scoring must be accurate and reliable without the need for secondary rounds of testing. Neither RFLP marker analysis nor microsatellite marker analysis for complex traits are amenable to high throughput analysis or scoring power. The scoring power of microsatellite markers is low, since the determination of whether a marker is present or absent requires highly skilled labor for reading gels because of the difficulty associated with distinguishing alleles at each locus on gels. The SNP haplotyping methods of the invention have high scoring power.

Linkage disequilibrium analysis is the preferential association within populations of one allele of one locus with another allele of another locus, at a frequency greater than that expected by chance. (Brookes, A. J, *Gene*, 234:177–186 (1999)). If a new polymorphic allele develops within a grouping of other polymorphic alleles at other contiguous loci and is so closely linked with these other alleles that recombination within that region is very unlikely, then, as the disease allele becomes replicated over time, all the alleles would be replicated together. Thus, linkage disequilibrium would have been established between the disease allele and the alleles within that grouping. This is important because the existence of linkage disequilibrium between polymorphic alleles would enable an allele of one polymorphic marker to be used as a beacon to locate the specific allele of another polymorphism. Linkage disequilibrium is a powerful tool that is useful in locating genes involved in the development of a complex trait. This tool can only be used, however, if the polymorphic markers are extremely stable and not prone to recombination events which would disrupt the DNA sequence of the polymorphic marker and very dense such that a sufficient number of markers will be found in a non-recombinatorial distance to the complex trait alleles, thereby assuring their association. SNPs are extremely stable and dense within the genome and thus have high statistical power as polymorphic markers for linkage disequilibrium studies.

The high throughput SNP haplotyping method of the invention overcomes many of the problems with the prior art methods of haplotyping. The methods of the invention which involve either capture of specific SNPs and/or solution phase detection are amenable to high throughput and allow the simultaneous discrimination and haplotyping of multiple SNP loci for both chromosomes of an individual. Methods can be performed on many nucleic acid samples at a time, thus, providing massive quantities of haplotype information, which is useful in characterizing complex traits and diseases. Additionally, the methods provide fewer false readings than some prior art methods.

In one aspect, the invention is a method for haplotyping, which involves the specific capture of a nucleic acid on the surface. The method involves analyzing a first polymorphic locus of a nucleic acid within a sample by specifically capturing the nucleic acid on a surface wherein the step of capturing the nucleic acid on the surface identifies a first allele of a first SNP of the polymorphic locus, repeating the analysis of the first polymorphic locus of the nucleic acid to identify a second allele of the first SNP of the polymorphic locus, analyzing a second SNP of a polymorphic locus of the nucleic acid sample to identify both alleles of the second SNP, and determining the haplotype based on the identification of each allele of each SNP.

Haplotyping is a process of genetic analysis which involves identifying genetic markers within a linked genetic region. The term haplotype is derived from the phrase "haploid genotype" and refers to the allelic constitution of a single chromosome or chromosomal region at two or more loci. The term has developed two variant uses in the field of human genetics. The first use of haplotype refers to the arrangement of alleles along a given section of a chromosome and is frequently used in association with disease mappings and studies to identify which closely linked polymorphic markers in a number of affected individuals are held in common by descent from a common ancestor who possessed the founder chromosome. The second use of the term haplotype refers to a small genetic region within which recombination is very rare, such that specific allelic combinations of polymorphic markers are seldom, if ever, disrupted by meiotic recombination. As a result, linkage disequilibrium exists and certain allelic recombinations will occur in the population much more frequently than would be expected by chance while other combinations will occur much less frequently. The haplotype analysis described herein is consistent with the second use of the term haplotype.

Thus the term "haplotype" as used herein, refers to an ordered combination of alleles in a defined genetic region that co-segregate. Such alleles are said to be "linked." The alleles of the haplotype may be within a gene, between genes, or in adjacent genes or chromosomal regions that co-segregate with high fidelity.

The term "linkage" refers to the degree to which regions of a nucleic acid are inherited together. DNA on different chromosomes are inherited together 50% of the time and do not exhibit linkage.

The term "linkage disequilibrium" refers to the co-segregation of two alleles at a linked loci such that the frequency of the co-segregation of the alleles is greater than would be expected from separate frequencies of occurrence of each allele.

In one method for SNP haplotyping, at least one of the two polymorphic loci is analyzed using a capture step. A nucleic acid within a sample is specifically captured on a surface in order to identify the first allele of a first SNP of the polymorphic locus. The nucleic acid can be captured by any method known in the art for sequence-specific nucleic acid capture. For instance, an allele-specific oligonucleotide (ASO) which is complementary to a sequence spanning the first SNP of the polymorphic locus of the nucleic acid may be attached to the surface then caused to interact with the nucleic acid by a hybridization reaction. Alternatively, any binding molecule, which is specific for the first SNP of the polymorphic locus of the nucleic acid, may be used to bind and interact with the nucleic acid to capture it on the surface. Additionally, a binding molecule, such as an ASO, which is linked to a first binding partner, such as streptavidin, may be allowed to hybridize or interact with the first SNP region of the nucleic acid within the sample to form a complex. This complex may then be interacted with a surface containing a second binding partner, such as biotin, attached thereto. Other methods for capturing a nucleic acid in a sequence-specific manner will be apparent to those of ordinary skill in the art. For instance primer extension, oligonucleotide ligation assay (OLA) or a combination of binding partner-ASO hybridization can be used.

Binding partner-ASO hybridization is a method which involves a tag attached to an ASO which can specifically hybridize to a nucleic acid. The tag is a binding partner which can specifically bind to another molecule and thus capture the ASO or ASO/nucleic acid complex. Binding partners include for instance biotin, avidin, flourescein, anti-flourescein antibodies, other antigens and antibodies, haptens, chemical groups which are capable of specifically interacting with specific compounds, nucleic acids that can specifically hybridize with nucleic acids attached to a surface.

The capture step is carried-out for each of the two alleles of the first SNP of the polymorphic locus of the nucleic acid in the sample. The capture steps performed on the first and second allele may be the same (i.e., both may involve allele-specific hybridization of the nucleic acid sample to an ASO attached to a surface) or different (i.e., analysis of the first allele may involve allele-specific hybridization and capture of the second allele may involve use of binding partners). It is important to identify using a capture step both the first and second alleles of the first SNP. Thus, it is important to determine the identity of both alleles of the first SNP within the nucleic acid sample.

Once the first two alleles of the first SNP are identified, both alleles of the second SNP are identified to determine the haplotype. The alleles of the second SNP may be determined using any methods known in the art for identifying SNPs. These methods include, but are not limited to, hybridization, primer extension, MALDI-TOF, HPLC, solution phase detection, and fluorescence detection.

Methods for identifying alleles of a SNP using hybridization include the methods described above. For instance, an ASO/nucleic acid sample complex, which is hybridized to a surface as described above, may be subjected to a second hybridization reaction to detect the identity of the second SNP in the nucleic acid sample. In this method, probes such as ASOs, which are complementary to both potential alleles of the second SNP, can be separately hybridized to the ASO/nucleic acid sample complex attached to the surface to identify the presence of the second SNP. If the probe or ASOs are labeled, the presence of the bound label can be detected to determine the presence or absence of the hybridization reaction.

Primer extension can also be used to identify the alleles of the second SNP. Primer extension is performed by hybridizing primers which flank but do not span the second SNP, performing a primer extension reaction to produce a PCR product. The primers may hybridize directly to the nucleic acid adjacent to the polymorphic site or they may hybridize to a site which is some distance away. It is possible to determine which allele is present in the nucleic acid sample in one of several ways. For instance, if one possible allele is a G at the polymorphic site then a labeled G can be added to the primer extension mixture instead of an unlabeled G. In some cases the labeled nucleotide is a dideoxynucleotide which will stop the production of the strand being created. The label may be any type of detectable label, e.g., a fluorescent label or a binding partner, e.g., biotin.

MALDI-TOF (matrix-assisted laser desorption ionization time of flight) mass spectrometry provides for the spectrometric determination of the mass of poorly ionizing or easily-fragmented analytes of low volatility by embedding them in a matrix of light-absorbing material and measuring the weight of the molecule as it is ionized and caused to fly by volatilization. Combinations of electric and magnetic fields are applied on the sample to cause the ionized material to move depending on the individual mass and charge of the molecule. U.S. Pat. No. 6,043,031, issued to Koster et al., describes an exemplary method for identifying single-base mutations within DNA using MALDI-TOF and other methods of mass spectrometry. Other methods are described in U.S. Pat. Nos. 6,002,127; 5,965,363; 5,905,259; 5,885,775; and 5,288,644, each of which is incorporated by reference.

HPLC (high performance liquid chromatography) is used for the analytical separation of bio-polymers, based on properties of the bio-polymers. HPLC can be used to separate nucleic acid sequences based on size and/or charge. A nucleic acid sequence having one base pair difference from another nucleic acid can be separated using HPLC. Thus, nucleic acid samples, which are identical except for a single allele may be differentially separated using HPLC, to identify the presence or absence of a particular allele. Preferably the HPLC is dHPLC (denatured HPLC). dHPLC involves the denaturation of the nucleic acid sample, followed be a reannealing step where the nucleic acid can assume a secondary structure, which will differ somewhat in nucleic acid samples having different alleles.

In some embodiments, the ASO or other probes or binding molecules is fixed to a surface. A surface, as used herein, refers to any type of solid support material to which a molecular component such as an ASO is capable of being fixed. Surfaces include, for instance, single or multi-well dishes, chips, slides, membranes, beads, agarose or other types of solid support mediums.

The nucleic acid sample being analyzed is any type of nucleic acid in which potential SNP-haplotypes exist. For instance, the nucleic acid sample may be an isolated genome or a portion of an isolated genome. An isolated genome consists of all of the DNA material from a particular organism, i.e., the entire genome. A portion of an isolated genome, which is referred to herein as a reduced complexity genome (RCG), is a plurality of DNA fragments within an isolated genome but which does not include the entire genome. Genomic DNA comprises the entire genetic component of a species excluding, applicable, mitochondrial and chloroplast DNA. Of course, the methods of the invention can also be used to analyze mitochondrial, chloroplast, etc., DNA as well. Depending on the particular species of the subject being analyzed, the genomic DNA can vary in complexity. For instance, species which are relatively low on the evolutionary scale, such as bacteria, can have genomic DNA, which is significantly less complex than species higher on the evolutionary scale. Bacteria, such as *E. coli* have approximately $2.4 \times 10^9$ grams/mol of haploid genome, and bacterial genomes having a size of less than about 5 million base pairs (5 megabases) are known. Genomes of intermediate complexity, such as those of plants, for instance, rice, have a genome size of approximately 700–1000 megabases. Genomes of highest complexity, such as maize or humans, have a genome size of approximately $10^9$–$10^{11}$. Humans have approximately $7.4 \times 10^{12}$ grams/mol of haploid genome.

The methods of the invention are useful for identifying haplotype information in subjects. A subject, as used herein, refers to any type of DNA-containing organism, and includes, for example, bacteria, virus, fungi, animals, including vertebrates, and invertebrates, and plants.

A "RCG" as used herein is a reproducible fraction of an isolated genome which is composed of a plurality of DNA fragments. The RCG can be composed of random or non-random segments or arbitrary or non-arbitrary segments. The term "reproducible fraction" refers to a portion of the genome which encompasses less than the entire native genome. If a reproducible fraction is produced twice or more using the same experimental conditions the fractions produced in each repetition include at least 50% of the same sequences. In some embodiments the fractions include at least 70%, 80%, 90%, 95%, 97%, or 99% of the same sequences, depending on how the fractions are produced. For instance, if a RCG is produced by PCR another RCG can be generated under identical experimental conditions having at a minimum greater than 90% of the sequences in the first RCG. Other methods for preparing a RCG such as size selection are still considered to be reproducible but often produce less than 99% of the same sequences.

A "plurality" of elements, as used throughout the application refers to 2 or more of the element. A "DNA fragment" is a polynucleotide sequence obtained from a genome at any point along the genome and encompassing any sequence of nucleotides. The DNA fragments of the invention can be generated according to any one of two types mechanisms, and thus there are two types of RCGs, PCR-generated RCGs and native RCGs.

The nucleic acid sample may be prepared using conventional PCR amplification of a polymorphic locus from a genomic DNA sample using known primers. Alternatively PCR-generated RCGs are randomly primed. That is, each of the polynucleotide fragments in the PCR-generated RCG all have common sequences at or near the 5' and 3' end of the fragment (When a tag is used in the primer, all of the 5' and 3' ends are identical. When a tag is not used the 5' and 3' ends have a series of N's followed by the TARGET sequence (reading in a 5' to 3' direction). The TARGET sequence is identical in each primer, with the exception of multiple-primed DOP-PCR) but the remaining nucleotides within the fragments do not have any sequence relation to one another. Thus, each polynucleotide fragment in a RCG includes a common 5' and 3' sequence which is determined by the constant region of the primer used to generate the RCG. For instance, if the RCG is generated using DOP-PCR (described in more detail below) each polynucleotide fragment would have near the 5' or 3' end nucleotides that are determined by the "TARGET nucleotide sequence". The TARGET nucleotide sequence is a sequence which is selected arbitrarily but which is constant within a set or subset (e.g. multiple primed DOP-PCR) of primers. Thus, each polynucleotide fragment can have the same nucleotide sequence near the 5' and 3' end arising from the same TARGET nucleotide sequence. In some cases more than one primer can be used to generate the RCG. When more than one primer is used, each member of the RCG would have a 5' and 3' end in common with at least one other member of the RCG and, more preferably, each member of the RCG would have a 5' and 3' end in common with at least 5% of the other members of the RCG. For example, if a RCG is prepared using DOP-PCR with 2 different primers having different TARGET nucleotide sequences, a population containing of four sets of PCR products having common ends could be generated. One set of PCR products could be generated having the TARGET nucleotide sequence of the first primer at or near both the 5' and 3' ends and another set could be generated having the TARGET nucleotide sequence of the second primer at or near both the 5' and 3' ends. Another set of PCR products could be generated having the TARGET nucleotide sequence of the second primer at or near the 5' end and the TARGET nucleotide sequence of the first primer at or near the 3' end. A fourth set of PCR products could be generated having the TARGET nucleotide sequence of the second primer at or near the 3' end and the TARGET nucleotide sequence of the first primer at or near the 5' end. The PCR generated genomes are composed of synthetic DNA fragments.

The DNA fragments of the native RCGs have arbitrary sequences. That is, each of the polynucleotide fragments in the native RCG do not have necessarily any sequence relation to another fragment of the same RCG. These sequences are selected based on other properties, such as size or, secondary characteristics. These sequences are referred to as native RCGs because they are prepared from native nucleic acid preparations rather than being synthesized. Thus they are native-non-synthetic DNA fragments. The fragments of the native RCG may share some sequence relation to one another (e.g. if produced by restriction enzymes). In some embodiments they do not share any sequence relation to one another.

In some preferred embodiments, the RCG includes a plurality of DNA fragments ranging in size from approximately 200 to 2,000 nucleotide residues. In a preferred embodiment, a RCG includes from 95 to 0.05% of the intact native genome. The fraction of the isolated genome which is present in the RCG of the invention represents at most 90% of the isolated genome, and in preferred embodiments, contains less than 50%, 40%, 30%, 20%, 10%, 5%, or 1% of the genome. A RCG preferably includes between 0.05 and 1% of the intact native genome. In a preferred embodiment, the RCG encompasses 10% or less of an intact native genome of a complex organism.

Several methods can be used to generate PCR-generated RCG including IRS-PCR, AP-PCR, DOP-PCR, multiple primed PCR, adaptor-PCR and multiple-primed-DOP-PCR. Hybridization conditions for particular PCR methods are selected in the context of the primer type and primer length to produce to yield a set of DNA fragments which is a percentage of the genome, as defined above. PCR methods have been described in many references, see e.g., U.S. Pat. Nos. 5,104,792; 5,106,727; 5,043,272; 5,487,985; 5,597,694; 5,731,171; 5,599,674; and 5,789,168. Basic PCR methods have been described in e.g., Saiki et al., *Science*, 230: 1350 (1985) and U.S. Pat. Nos. 4,683,195, 4,683,202 (both issued Jul. 18, 1987) and U.S. Pat. No. 4,800,159 (issued Jan. 24, 1989).

Another method for generating RCGs is based on the development of native RCGs. Several methods can be used to generate native RCGs, including DNA fragment size selection, isolating a fraction of DNA from a sample which has been denatured and reannealed, pH-separation, separation based on secondary structure, etc.

Size selection can be used to generate a RCG by separating polynucleotides in a genome into different fractions wherein each fraction contains polynucleotides of an approximately equal size. One or more fractions can be selected and used as the RCG. The number of fractions selected will depend on the method used to fragment the genome and to fractionate the pieces of the genome, as well as the total number of fractions. In order to increase the complexity of the RCG, more fractions are selected. One method of generating a RCG involves fragmenting a genome into arbitrarily size pieces and separating the pieces on a gel (or by HPLC or another size fractionation method). A portion of the gel is excised, and DNA fragments contained in the portion are isolated. Typically, restriction enzymes can be used to produce DNA fragments in a reproducible manner.

Different nucleic acid sources may be used to generate RCGs. For instance, mitochondrial DNA can be isolated and used as the source of the RCG.

Separation based on secondary structure can be accomplished in a manner similar to size selection. Different fractions of a genome having secondary structure can be separated on a gel. One or more fractions are excised from the gel, and DNA fragments are isolated therefrom.

Another method for creating a native RCG involves isolating a fraction of DNA from a sample which has been denatured and reannealed. A genomic DNA sample is denatured, and denatured nucleic acid molecules are allowed to reanneal under selected conditions. Some conditions allow more of the DNA to be reannealed than other conditions. These conditions are well known to those of ordinary skill in the art. Either the reannealed or the remaining denatured fractions can be isolated. It is desirable to select the smaller of these two fractions in order to generate RCG. The reannealing conditions used in the particular reaction determine which fraction is the smaller fraction. Variations of this method can also be used to generate RCGs. For instance, once a portion of the fraction is allowed to reanneal, the double stranded DNA may be removed (e.g., using column chromatography), the remaining DNA can then be allowed to partially reanneal, and the reannealed fraction can be isolated and used. This variation is particularly useful for removing repetitive elements of the DNA, which rapidly reanneal.

The amount of isolated genome used in the method of preparing RCGs will vary, depending on the complexity of the initial isolated genome. Genomes of low complexity, such as bacterial genomes having a size of less than about 5 million base pairs (5 megabases), usually are used in an amount from approximately 10 picograms to about 250 nanograms. A more preferred range is from 30 picograms to about 7.5 nanograms, and even more preferably, about 1 nanogram. Genomes of intermediate complexity, such as plants (for instance, rice, having a genome size of approximately 700–1,000 megabases) can be used in a range of from approximately 0.5 nanograms to 250 nanograms. More preferably, the amount is between 1 nanogram and 50 nanograms. Genomes of highest complexity (such as maize or humans, having a genome size of approximately 3,000 megabases) can be used in an amount from approximately 1 nanogram to 250 nanograms (e.g. for PCR).

In other aspects of the invention, the nucleic acid sample can be an entire or a portion of an RNA genome. RNA genomes differ from DNA genomes in that they are generated from RNA rather than from DNA. An RNA genome can be, for instance, a cDNA preparation made by reverse transcription of RNA obtained from cells of a subject (e.g. human ovarian carcinoma cells). Thus, an RNA genome can be composed of DNA sequences, as long as the DNA is derived from RNA. RNA samples can also be used directly.

Each of the types of nucleic acid samples set forth herein is described in more detail in co-pending U.S. patent application Ser. No. 09/404,912, filed on Sep. 24, 1999, which is hereby incorporated by reference.

The methods of the invention involve analysis of at least two SNPs to identify the haplotype. The two SNPs are referred to as SNP1 or the first SNP and SNP2 or the second SNP. The reference to a first or second SNP does not provide an indication of the order of the SNPs on the nucleic acid. A "single nucleotide polymorphism" or "SNP" as used herein is a single base pair (i.e., a pair of complementary nucleotide residues on opposite genomic strands) within a DNA region wherein the identities of the paired nucleotide residues vary from individual to individual. At the variable base pair (alleles) in the SNP, two or more alternative base pairings can occur at a relatively high frequency in a subject, (e.g. human) population.

A "polymorphic region" is a region or segment of DNA the nucleotide sequence of which varies from individual to individual. The two DNA strands which are complementary to one another except at the variable positions are referred to as alleles. A polymorphism is allelic because some members of a species have one allele and other members have a variant allele and some have both. When only one variant sequence exists, a polymorphism is referred to as a diallelic polymorphism. There are three possible genotypes in a diallelic polymorphic DNA in a diploid organism. These three genotypes arise because it is possible that a diploid individual's DNA may be homozygous for one allele, homozygous for the other allele, or heterozygous (i.e. having one copy of each allele). When other mutations are present, it is possible to have triallelic or higher order polymorphisms. These multiple mutation polymorphisms produce more complicated genotypes.

A "polymorphic locus", as used herein, refers to a region of a nucleic acid that includes more than one single nucleotide polymorphism.

In one embodiment, the method for haplotyping involves a bi-phasic allele-specific oligonucleotide hybridization technology. Briefly, the method is carried out as shown in FIG. 1 for a haplotype consisting of two SNP loci. During the first phase of the method, a SNP1 allele-specific oligonucleotide (ASO) is synthesized and attached to a surface. A nucleic acid sample is then prepared using a method such as amplification of a genome to produce a nucleic acid sample containing the polymorphic locus. Optionally, the nucleic acid sample can be labeled. The sample is then allowed to hybridize to the SNP1 ASO coated on the surface to produce a SNP1/nucleic acid sample complex. Excess is removed. In Phase 2 a SNP2 ASO, which is labeled is synthesized and allowed to hybridize to the SNP1 ASO/nucleic acid sample complex. The entire surface is then scanned and the haplotype can be scored. The SNP1 ASO is actually a set of ASO which includes two allele-specific oligonucleotides corresponding to an anti-sense version of each allele of two SNPs of a polymorphic locus. The second set of ASOs corresponds to the second SNP (SNP2) of the polymorphic locus. In the method, the nucleic acid sample will only hybridize to the ASO of the first set of ASOs, which is anti-sense to the allele of the first SNP in the genomic sample. Likewise, only the ASO of the second set of ASOs, which is anti-sense to the allele of the second SNP present in the nucleic acid sample, will hybridize. These haplotyping methods for identifying 2 SNPs generally involve the analysis of 4 wells. If a subject is homozygous, analysis of their DNA will result in a signal in one well. If a subject is heterozygous, analysis of their DNA will result in a signal in two wells.

In general, the high throughput SNP haplotyping methods of the invention are useful in linkage disequilibrium studies for the analysis of complex traits to localized genes involved in diseases such as diabetes, multiple sclerosis, and asthma; diagnostic analysis to determine the presence or absence of a predisposing disease haplotype or other trait; pharmacogenomic analysis to identify haplotypes that correlate with either positive or negative responses to drugs and development; genome-wide scan studies for complex trait analysis using SNP haplotypes, instead of single SNPs, to increase the statistical power; etc.

Deletions, multiplications, or substitutions in genes can result in genetic disease. Most of these deletions, multiplications, or substitutions, causing multiple alleles, produce indistinguishable or distinguishable "normal" phenotypes. For instance, multiple alleles produce variable characteristics like eye color. Some genetic alterations, however, are associated with clinical disease like sickle cell anemia. The haplotyping methods of the invention are useful for identifying both normal phenotypes and disease phenotypes. Thus, the methods for the invention are useful for identifying traits such as eye color as well as for diagnostics to determine presence or absence of predisposing disease haplotype in a subject. Some diseases which are known to have a genetic element include colon cancer, breast cancer, cystic fibrosis, neurofibromatosis type 2, LiFraumeni disease, VonHippel-Lindau disease, thalassemia, ornithine, transcarbamylase deficiency, hypoxanthine-guanine-phosphoribosyl-transferase deficiency, phenylketonuria, etc.

Another recently identified phenomenon is that the inheritance of varying haplotypes within the same gene can alter a disease phenotype altogether. This is exemplified by polymorphic mutations in the prion gene, PrP. (Goldfarb, L. G. and Petersen, R. B., Science, 258:806–808 (1992)). Individuals that inherit a SNP polymorphism at codon 178 of the PRP gene, will develop a Creutzfeldt-Jakob disease. If the individual also inherits a concomitant SNP polymorphism at codon 129 of the PRP gene, then that individual will develop a fatal familial insomnia instead. Therefore, the precise haplotype inherited can change the effect of the mutations involved, resulting in distinctly different phenotypic diseases. The methods of the invention are useful for making these types of distinctions.

Identification of haplotypes associated with phenotypic traits is useful for many purposes in addition to identifying predisposition to disease. For example, identification of a correlation between susceptibility to a particular drug or a therapeutic treatment and specific genetic alterations is particularly useful for tailoring therapeutic treatments to a specific individual. The methods are also useful in prenatal screening to identify whether a fetus is afflicted with or is predisposed to develop a serious disease. Additionally, this type of information is useful for screening animals or plants bred for the purposes of enhancing or exhibiting desired characteristics.

Other methods for high throughput haplotyping, according to the invention, involve the identification of SNPs in solution. In one aspect the invention is a method for haplotyping by analyzing a genotype of a first SNP of a polymorphic locus of a nucleic acid within a sample in solution by detecting the presence or absence of a first labeled probe which specifically identifies a first putative allele of the SNP and detecting the presence or absence of a second labeled probe which specifically identifies a second putative allele of the SNP, separating the nucleic acid sample based on the genotype of the first SNP, and analyzing a second SNP of the polymorphic locus of the separated nucleic acid samples to identify the haplotype of the nucleic acid.

The first and second allele of the first SNP of the polymorphic locus are detected in solution using labeled probes. The labeled probes are any type of molecule which specifically binds to one allele of the SNP and not the other and which include a detectable label. The molecule which specifically interacts with one of the two alleles can be any type of molecule, for instance, it may be a DNA-specific binding protein or an ASO complementary to the allele containing DNA. A label may be a light-emissive label, radioactive label, etc. Light-emissive labels can be added to the molecule or may be naturally-occurring within the molecule. For instance, some bases of a nucleotide are naturally-occurring light-emissive labels. In the case when a naturally-occurring light-emissive label is used, an extrinsic label does not need to be added to the molecule. Light-emissive labels, which can be added to molecules include fluorophors and quenchers, light-scattering particles (such as gold particles which scatter light), etc. Radioactive labels include, but are not limited to, $^3$H, $^{32}$P, and $^{35}$S. The use of each of these types of labels is well-known to those of ordinary skill in the art.

Once the first SNP has been identified using a labeled probe, the nucleic acid sample is separated such that the DNA molecules containing the first allele are in a separate container from the DNA samples containing the second allele. One method for accomplishing this separation is through the use of flow cytometry e.g., using a fluorescence-activated cell sorter (FACS). Flow cytometry analysis involves the separation of single molecules based on the presence of a particular fluorescence marker. Thus, a nucleic acid molecule which includes a labeled probe that emits in the red light wavelength will be separated from the nucleic acid molecules hybridized to a labeled probe which emits light in the green wavelength. Once the two samples are separated, each can be separately analyzed to identify the presence or absence of an allele at the second SNP. Other methods for separating the nucleic acid samples based on the allele present in the sample, include but are not limited to (1) the use of an ASO attached to different size beads which can be separated by size, affinity, or weight, and (2) the use of tags such as binding partners which can be separated based on their specific binding interactions.

In other aspects, the invention involves solution phase analysis that utilizes four labeled probes, each specific for an allele of the two SNPS. In this analysis, the labeled probes are allowed to interact with the nucleic acid sample to form complexes. The labeled complexes are then separated such that each nucleic acid complex is separate from one another. Thus, this analysis is based on single molecule detection strategies. Each individual nucleic acid is separated from other nucleic acid molecules. The separate nucleic acid molecules are then detected for the presence or absence of each of the four labeled probes.

Figure 4:
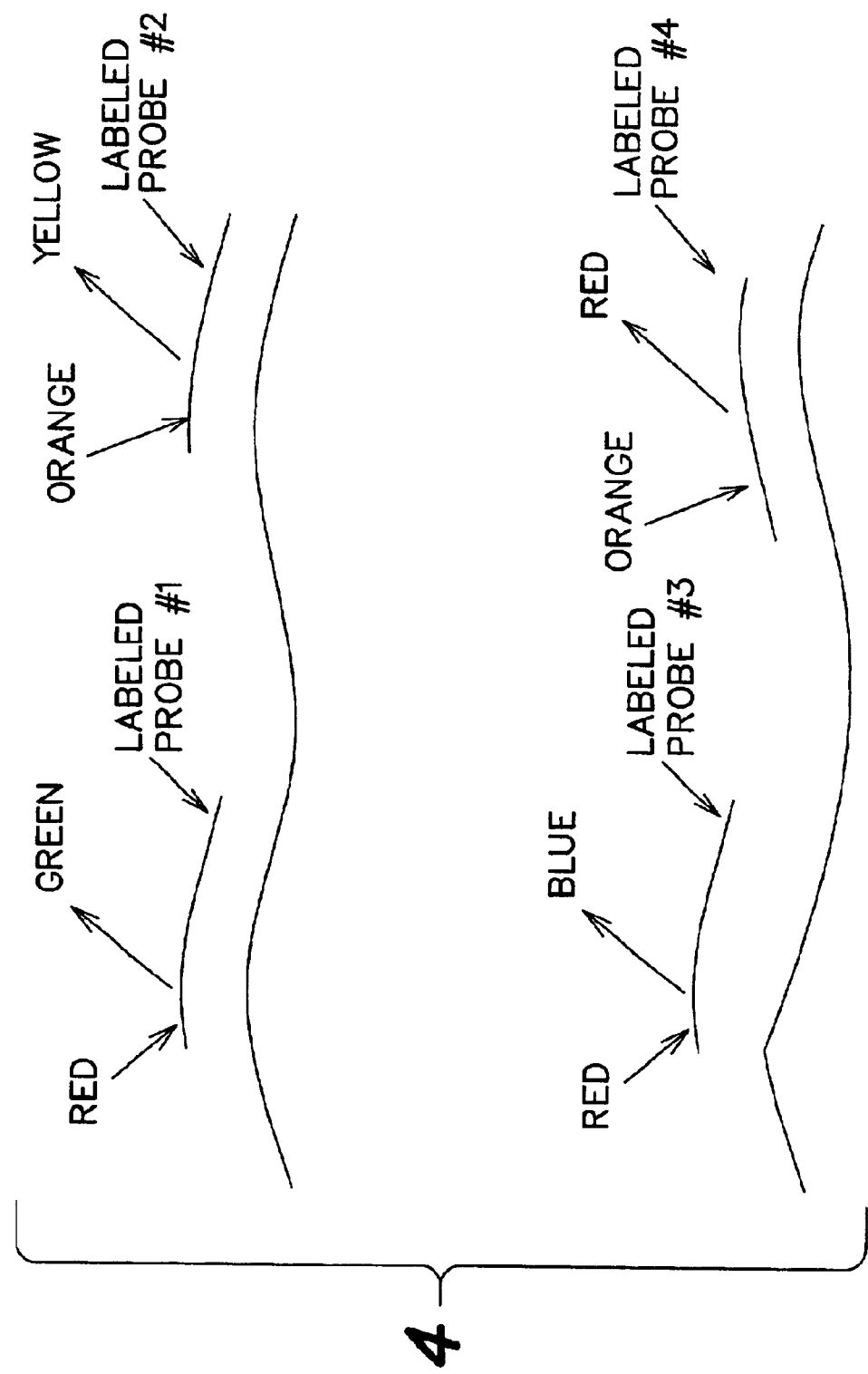
FIG. 4 is a diagram depicting examples of nucleic acid samples labeled with different fluorescent labels, to exemplify the single molecule detection methods.

The method can be accomplished, for example, as shown in the schematic diagram of FIG. 4. In the figure, it is shown that each single nucleic acid sample, which has been separated, includes two of the four labeled probes, one specific for a first allele of the first SNP and the other specific for an allele of the second SNP. In the examples shown, the first labeled probe includes a label which is stimulated in the red wavelength of light to produce a signal detected in the green wavelength. The second labeled probe is capable of detecting light in the orange wavelength and emitting light in the yellow wavelength. The single molecule, when subjected to light within the red wavelength spectrum, will emit green light that can be detected. Likewise, the sample, when exposed to light within the orange wavelength, will emit yellow light. Thus, if the sample, when exposed to red and orange light, emits green and yellow, this is indicative that the first and third labeled probes, specifically identifying the first allele of the first SNP and the first allele of the second SNP are present. Alternatively, when light of red and orange wavelengths are used to stimulate the sample and blue and red light wavelengths are emitted, this is indicative that the second and fourth labeled probes have bound to the nucleic acid sample, thus identifying the presence of the second allele of the first SNP and the second allele of the second SNP. Other combinations would be indicative of other haplotypes which are possible in this two SNP system. Other combinations of labels can be used. For instance, each of the 4 labeled probes can be labeled with a molecule that is stimulated in one wavelength of light, e.g., red, as long as each labeled probe emits in a different spectrum (or one may quench). Alternatively, each of the 4 labeled probes can be labeled with a molecule that is stimulated by distinct wavelengths of light, but all can emit in the same or different spectrums.

In some preferred embodiments fluorescence detection of single molecules is used to identify the components of the polymorphic locus. A fluorescent label or fluorophore is a substance which is capable of exhibiting fluorescence within a detectable range. Fluorophores include, but are not limited to, fluorescein, isothiocyanate, fluorescein amine, eosin, rhodamine, dansyl, umbelliferone, 5-carboxyfluorescein (FAM), 2'7'-dimethoxy-4'5'-dichloro-6-carboxyfluorescein (JOE), rhodamine, 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2' disulfonic acid, acridine, acridine isothiocyanate, r-amino-N->3-vinylsulfonyl) phenyl!naphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumaran 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron. RTM. Brilliant Red 3B-A), lissamine rhodamine B sulfonyl chloride, rhodamine B, rhodamine 123, rhodamine X isothiocyanate, sulforhodamine B, sulforhodamine 101, sulfonyl chloride derivative of sulforhodamine 101, (Texas Red), tetramethyl rhodamine, tetramethyl rhodamine isothiocyanate (TRITC), riboflavin, rosolic acid, and terbium chelate derivatives.

Fluorescence is measured using a fluorometer. The optical emission from the fluorescence molecule can be detected by the fluorometer and processed as a signal. When fluorescence is being measured in a sample fixed to various portions of the surface, the surface can be moved using a multi-access translation stage in order to position the different areas of the surface, such that the signal can be collected. Many types of flourometers have been developed. For instance, a new sensitive instrument for measuring FRET is described in U.S. Pat. No. 5,911,952.

In other aspects the invention is a method for haplotyping which is accomplished by performing four hybridization reactions on a nucleic acid sample, each of the four hybridization reactions involving one ASO specific for one allele of one of two SNPs, each of the ASOs labeled with a spectrally distinct label and wherein each label on the ASO specific for a first of the two SNPs is a spectral pair with the label on each ASO specific for the second of the two SNPs, bringing each of the labeled ASOs in each hybridization reaction within energy transfer distance from one another, exciting one of the labeled ASOs in each hybridization reaction, and detecting light released from the other labeled ASO as a signal, wherein the presence or absence of a signal for each hybridization reaction is an indicator of the haplotype of the nucleic acid sample.

A process referred to as a molecular beacon for nucleic acid detection has previously been described. The method involves the use of a probe which is in the form of a stem loop structure, such that the 3' and 5' ends of the nucleic acid probe are adjacent one another in the stem section. The 5' and 3' ends are labeled with a donor fluorophore and a quencher. When this probe encounters a complementary nucleic acid within the sample, the secondary structure stem loop is destabilized and the 5' and 3' ends are moved away from one another. This causes the fluorescent group to emit light which is no longer quenched and thus an increase in fluorescence emission occurs. (Discussed in U.S. Pat. No. 5,989,823). This type of analysis has been used in the detection of alleles within a nucleic acid sample. (Kostrikis, et al., *Science*, 279:1228–1229 (1998) and Tyagi, et al. (1998), *Nature Biotechnology* 16:49–53)).

This method is similar to the methods of the invention, except that binding partners are used to bring the fluorophores within proximity of one another. Binding partners are two molecules which specifically interact with one another when brought into proximity with one another. Many types of binding partners are known in the art. Some well known examples of a binding partners are biotin and avidin or streptavidin, as well as antibody and antigen. These binding partners are used to bring the regions of the nucleic acid housing the two SNPs within proximity of one another. For instance, the first SNP may be labeled with an ASO which is conjugated to biotin. The second SNP may be hybridized with an ASO which is conjugates to avidin. Either the biotin or the avidin may contain fluorophores, which when brought within proximity of one another, will produce a signal or the ASO may contain the fluorophore label which would be brought in proximity with the other fluorophore label when the biotin and avidin interact.

Streptavidin and biotin labeled with various fluorophores are commercially available from several sources including Molecule Probes (Eugene, Oreg.), Intergen (Purchase, N.Y.) and NEN (Boston, Mass.).

Fluorescence resonance energy transfer (FRET) is the transfer of electronic excitation energy by the Forster mechanism. FRET is useful for measuring the distance between a pair of fluorophores (donor and acceptor) which are in a range of 10–80 angstroms from one another. FRET has previously been used to study the hybridization of complementary oligodeoxynucleotides (Cardullo et al., *PNAS, USA*, 85:8790–8794 (1988)), and various other binding assays.

FRET arises from certain fluorophores which when excited by exposure to a particular wavelength of light will emit light at a different wavelength. A donor fluorophore absorbs a photon of energy and transfers this energy non-radiatively to the acceptor fluorophore. When the excitation and emission spectra of two fluorophores which are brought within close proximity of one another overlap, the excitation of one fluorophore will cause it to emit light at a wavelength that is absorbed and that can stimulate the second fluorophore causing it to fluoresce. During this process, the fluorescence of the donor molecule is quenched and fluorescence intensity of the acceptor molecule is enhanced. If the donor is in proximity with a fluorophore which is a non-acceptor (referred to as a quencher), the fluorescence of the donor is still quenched but there is no subsequent emission of fluorescence by the second fluorophore, or quencher. Thus, there is no emission of light.

When selecting fluorophores for FRET analysis several parameters can be considered. U.S. Pat. No. 4,996,143 describes some of the parameters that should be considered when designing fluorescent probes, such as the spacing of the fluorescent moieties and the length of the portion of the molecule which connects the fluorescent moiety to the base unit of the nucleic acid. In order for FRET to occur, the donor and acceptor molecules should be within 100 angstroms of one another. When attached to nucleic acids, preferably, the donor and acceptor fluorophores are within 1 to 20 base pairs of one another for FRET analysis. Additionally, when performing FRET analysis flourophores which are spectral pairs should be used. Two fluorophores are spectral pairs when one of the two fluorophores emits light at a wavelength which either causes the other fluorophore to emit light of a different wavelength or to quench the light emitted by the first fluorophore without producing additional light. For instance FAM is excited by light with a wave-length of approximately 488 nm and emits light with a spectrum of 500–650 nm. Thus, FAM is a suitable donor fluorophore for use with JOE, TAMRA and ROX, all of which have an excitation maximum of 514 nm and a spectral pair is formed when FAM is matched with either JOE, TAMRA or ROX. Appropriate spectral pairs among the known flourophores are well known to those of ordinary skill in the art.

EXAMPLES

Example 1

Haplotyne Analysis of Multiple Individuals Using a Double Hybridization Method

Two single nucleotide polymorphisms (spaced 212 nucleotides apart) commonly occur in the dopamine $D_2$ receptor gene. SNP1 is a T to G transversion at nucleotide 3208 and SNP2 is a C to T transition at nucleotide 3420 (Sarkar, G., et al., *Genomics*, 11:8–14 (1991)).

These polymorphisms were shown to be common in all races examined, with allele frequencies ranging from 39% to 49% (Sarkar, G., et al., *Genomics*, 11:8–14 (1991)). This system has been previously used to demonstrate the 3' mismatch PCR-SSP haplotyping technique (Sarkar, G., et al., *Biotechniques*, 10:437–440 (1991)). This system is also ideal for demonstrating the efficacy of the SNP-Haplotyping Method of the invention for the following reasons:

1. These polymorphisms are commonly represented in the population, i.e. exhibit high allele frequencies.
2. They are in close proximity to one another facilitating the generation of PCR products containing both polymorphisms from test genomes.
3. They exhibit no linkage disequilibrium such that no single haplotype at this locus dominates in the population.

1. Verification of the Double Hybridization SNP-Haplotyping Method

To verify the feasibility, efficacy and reliability of the SNP-Haplotyping Method, haplotypes at the $D_2$ receptor locus are determined for multiple individuals, using standard sequence analysis. The haplotypes determined by sequence analysis are used for comparison to the haplotypes determined by the SNP-Haplotyping Method of the invention.

The sequencing step is performed as follows:

1. Primer 1 ($M13^{(For)}$--CCTCAGTGACATCCTTGCCT) (SEQ ID NO:1) and Primer 2 ($M13^{(Rev)}$ CATGCCCATTCTTCTCTGGT) (SEQ ID NO:2) flank the region containing SNP1/SNP2 of the $D_2$ receptor polymorphic locus. Primer 1 contains an M13 forward sequence at the 5' end and Primer 2 contains an M13 reverse sequences at the 5' end to facilitate sequencing of the PCR products. The expected size of the PCR product is 350 base pairs.
2. DNA from unrelated individuals is obtained from the National Human Genome Research Institute (NHGRI) which is a database containing a standardized collection of DNA from 450 unrelated individuals. Primers 1 and 2 are used to PCR amplify the polymorphic locus from the $D_2$ receptor gene from all of the individuals using a proof-reading thermostable DNA polymerase such as Pfu polymerase, as previously described (Sarkar, G., et al., *Genomics*, 11:8–14, (1991)).
3. Each of the PCR reactions is separated by agarose gel electrophoresis and the PCR products cut from the gel and purified. These purified PCR products represent the $D_2$ receptor polymorphic locus from the individuals.
4. The genotype of the polymorphic locus for each individual is determined by sequencing an aliquot of each purified PCR product using dye-labeled M13 forward and reverse primers.
5. The haplotype of the polymorphic locus for each individual is determined as follows:
   a) An aliquot of each purified PCR product is subcloned into a plasmid vector such as TA vector (Invitrogen), and transformed into the appropriate strain of *E. coli*. This results in multiple transformations, one for each individual.
   b) Six colonies are picked from each transformation and plasmid DNA is isolated from all colonies. Picking 6 colonies/transformation results in a >96% chance that the loci from both chromosomes (alleles) of each individual is represented and therefore analyzed.
   c) The plasmid inserts, representing the $D_2$ receptor polymorphic locus for each individual, are sequenced using vector-specific primers. The sequences are analyzed to determine the haplotype of the SNP1/SNP2 locus for each of the individuals.

Genotypes

Nine combinations of (SNP1: SNP2) genotypes are possible for the two SNP loci and each of the tested individuals is expected to possess one of the following:

| G/T:C/T | G/G:C/T | T/T:C/T |
| G/T:C/C | G/G:C/C | T/T:C/C |
| G/T:T/T | G/G:T/T | T/T:T/C |

Haplotypes

Four haplotypes of the two SNP loci (SNP1=G/T and SNP2+C/T) are possible:

| Haplotype I (G-C) | Haplotype III (T-C) |
| Haplotype II (G-T) | Haplotype IV (T—T) |

Each chromosome will have its own haplotype for the two SNP loci, therefore, each individual is expected to possess two haplotypes. Since the maternal and paternal chromosomes cannot be distinguished, ten possible haplotype combinations between the two chromosomes are possible and each individual is scored as possessing one of the following haplotype combinations:

| I, I   | II, II  | III, III | IV, IV |
| I, II  | II, III | III, IV  |        |
| I, III | II, IV  |          |        |
| I, IV  |         |          |        |

2. Genotype Analysis of a Single Locus (the SNP1 Locus of the D2 Receptor Gene) Using Phase I Allele-Specific Oligonucleotide Hybridization on Immobilized SNP1 Allele-Specific Oligonucleotides The SNP-Haplotyping Method of the invention depends, in some aspects, on the ability to discriminate between polymorphic loci using differential ASO hybridizations. The technique of ASO hybridization has been established in the literature (Wang, D., et al., *Science*, 280:1077–1082 (1998); Guo, S., et al., *Nucleic Acids Res.*, 22:5456–5465 (1994); Sapolsky, R., et al., *Genet. Anal. Biomed, Engin.* 14:187–192 (1999)). Phase I of this method involves the accurate genotyping of multiple individuals, for the SNP1 locus, using ASO hybridization techniques. The following protocol is outlined in FIG. 1, which outlines Phase I Hybridization Protocol and Expected Results.

Step 1: Synthesis of anti-sense SNP1 allele-specific oligonucleotides

Step 2: Attachment of anti-sense SNP1 allele-specific oligos to wells

Step 3: Amplification of the SNP1/SNP2 polymorphic Locus from individuals using a Cy3-labeled PCR reaction Step 4: Hybridization of Cy3-labeled PCR products from each individual to duplicate SNP1 (G) allele wells and duplicate SNP1-(T) allele wells Step 1 involves Synthesis of Oligonucleotides Representing the Antisense Strand of the Two SNP1 Alleles. Two oligonucleotides are synthesized, each representing one allele of the SNP1 (G/T) locus of the $D_2$ receptor. The oligonucleotides represent the antisense (complementary) strand for each allele as follows:

SNP1-(G detecting) oligo:
$NH_2$-(T)$_{15}$AGTCTCCC(C)TTTCCCT    (SEQ ID NO:3)

SNP1-(T detecting) oligo:
$NH_2$-(T)$_{15}$AGTCTCCC(A)CTTTCCCT    (SEQ ID NO:4)

The amino group is added to facilitate binding to the surface of the wells. The addition of 15 Ts on the 5' end of the oligonucleotide functions as a "spacer" sequence. Spacer sequences have been shown to greatly enhance the hybridization signal, presumably by lifting the hybridization sequence off the support surface thereby decreasing the steric interference produced by that surface (Guo, S., et al., *Nucleic Acids Res.*, 22:5456–5465 (1994)), but are not essential.

Step 2 involves Binding of Oligonucleotides to Solid Surface. Each oligonucleotide is covalently attached to one 96-well Xenobind Black plate (Xenopore, Corp., Hawthorne, N.J.) as follows:

a) 200 pmol of each oligonucleotide is resuspended in 0.05 M phosphate buffer, pH 7.0 and placed into the wells of a Xenobind plate. One plate contains SNP1-(G-detecting) oligos and the second plate contains SNP1-(T detecting) oligos.

b) Plates are incubated at 37° C. for 2 hours.

c) Plates are washed once with 0.2% SDS and twice with dd$H_2$O.

d) Unbound sites are blocked with blocking solution (1 g sodium borate in 400 mls of 25% ethanol in PBS) for 5 minutes.

e) Wells are washed, as above, and air dried in the dark at room temperature.

Step 3 involves Amplification of the Polymorphic Locus from the Test Subjects. The polymorphic locus (SNP1 and SNP2) from the receptor gene is PCR-amplified from each of the individual test subjects. The primers used are the primers outlined above (SEQ ID NO:1 and 3), except that the M13 sequences are omitted. The PCR is carried out in the presence of Cy3-dCTP, to fluorescently label the products, and the PCR products are purified using a PCR purification column system (QIAGEN).

Step 4 involves Hybridization of the Polymorphic Locus PCR Products from the Individual Test Subjects to the SNP1-(G-detecting) oligo and SNP1-(T detecting) oligo bound wells.

a) Each of the 48 fluorescently labeled PCR products is denatured by boiling and diluted to 0.5 pmol/ml of TMAC hybridization solution (3.0 M TMAC/0.6% SDS/10 mM sodium phosphate pH 6.5/5×Denhardt's solution/40 ug/ml yeast tRNA). TMAC (Sigma, Inc.) allows the hybridizations to progress independent of G/C content and intrinsic melting temperatures.

b) 200 $\mu$l each of the diluted PCR products is added in duplicate to two wells (#of individuals (i.e. 48 individuals)×2 wells=96 wells) of the SNP1-(G detecting) oligo plate and two wells of the SNP1-(T detecting) oligo plate.

Hybridizations are incubated overnight at 52° C. with gentle agitation.

c) Plates are washed twice for 30 minutes at room temperature and once for 20 minutes at 54° C. in wash buffer (3.0 M TMAC/0.6% SDS/10 mM sodium phosphate, pH 6.8)

d) Plates are read on an Ultra Reader fluorescent microplate reader (Tecan Instruments) to determine which wells have a positive hybridization signal.

Control wells are set up to monitor background produced by non-specific binding to unattached sites of the wells, insufficient blocking, random DNA/DNA interactions etc. To control for and subtract out background signals from the ASO hybridizations, a random segment of human DNA is amplified from genomic DNA. This random segment is of equal length (350 base pairs) and of approximately equal G/C and A/T content to the locus specific PCR products from the test individuals. These control DNA segments are hybridized to wells bound with each of the SNP1 allele-specific oligos as outlined above.

If the Cy3-labeled PCR product from an individual binds to the oligonucleotides attached to the wells, then a fluorescent signal is detected in that well. If the PCR product does not bind to the oligonucleotide attached to the well, then no fluorescent signal is detected. The following genotypes are possible:

a) G/T heterozygote
b) G/G homozygote
c) TT homozygote

The hybridization pattern for each genotype are described for the possible hybridization patterns expected for the SNP1 (G/T) locus of the D2 receptor gene. G/T heterozygote, G/G homozygote, T/T homozygote.

1. G/T Heterozygote: If an individual is a G/T heterozygote then the hybridization of the Cy3-labeled PCR product occurs in wells containing both the SNP-1(G detecting) oligo and the SNP1-(T detecting) oligo. As a result a fluorescent signal is detected for wells bound with oligonucleotides representing both SNP1 alleles.
2. G/G Homozygote: If an individual is a G/G homozygote then the hybridization of the Cy3-labeled PCR product occurs only in the wells containing the SNP1-(G detecting) oligo. As a result, a fluorescent signals are detected only in wells bound with oligonucleotides representing the SNP1-G allele.
3. T/T Homozygote: If an individual is a T/T homozygote then the hybridization of the Cy3-labeled PCR product occurs only to the wells containing the SNP1-(T detecting) oligo. As a result, a fluorescent signal is detected only in wells bound with oligonucleotides representing the SNP1-allele.

Control Wells: Negligible fluorescent signals are obtained with wells hybridized with control PCR products. Any background signal is subtracted from the fluorescent signals obtained with the test wells and these values are used as the adjusted results.

The conditions outlined herein, particularly the use of TMAC in the hybridization reactions, have been shown to accurately discriminate single base mismatches in ASO hybridizations. In order to minimize any potential indiscriminate binding in the reaction the following optional steps can be performed.

1. Cold competitor (unlabeled oligos of the opposite allele) is added to the hybridization reactions to compete-out binding to the indiscriminate allele.
2. Enhanced discrimination of SNPs by artificial mismatch hybridization can also be used (Guo, Z., et al., *Nature Biotech*, 15:331–335 (1997)). It has been shown that the ability to discriminate between 1 vs. 2 mismatches is 200% greater than the discrimination between 0 vs. 1 mismatch. Therefore, the difference in stability of hybridized DNA segments with 2 mismatches versus 1 mismatch is significantly greater than the stability differences between 0 mismatches and 1 mismatch. Therefore, the addition of an artificial mismatch into the SNP1 allele-specific oligonucleotides bound to the wells, can be expected to abolish any non-specific binding between an individual's SNP1 locus and the erroneous SNP1-specific allele oligonucleotide.

3. Haplotype Analysis of Two Loci (the SNP1 and SNP2 Loci of the D2 Receptor Gene) Using Phase I and II Allele-Specific Oligonucleotide Hybridization on Immobilized SNP1 Allele-Specific Oligonucleotides Phase I of the Method of Haplotyping (outlined above) involves hybridizing CY3-labeled PCR products from the SNP1/SNP2 loci of each individual to SNP1 allele-specific oligonucleotides. Phase II involves an additional hybridization with SNP2 allele-specific oligonucleotides which simultaneously determines: 1) the genotype of the SNP2 locus for each individual and 2) the phase of the SNP2 genotype with the SNP1 genotype, in other words, the haplotype.

SNP1 Antisense Allele-specific Oligonucleotides are bound to the Wells of a Xenobind Black 96-Well Plate. SNP1-(G)-detecting and SNP1-(T)-detecting antisense allele-specific oligonucleotides (SEQ ID NO:3 and 4) are synthesized. Each SNP1 oligo is bound to two 96 well Xenobind Black plates (4 plates total) as outlined above.

PCR Amplification and Phase I Hybridization of the SNP1/SNP2 Locus from the Individual Test Subjects to the SNP1-(G detecting) Oligo and SNP1-(T detecting) Oligo Bound Wells is performed. The SNP1/SNP2 locus is PCR amplified from the test subjects in the presence of Cy3-dCTP and hybridized to two wells each of the 4 plates containing immobilized SNP1 (G) or (T) allele-specific oligos. However, after the last wash at 54° C., the plates are not read on a fluorometer. They are, instead, subjected to the next Step in the SNP-Haplotyping Protocol.

Synthesis of Oligonucleotides Representing the Antisense Sequence of the Two SNP2 Alleles is performed next. Phase II Hybridization to the Immobilized SNP1 allele-specific oligo:SNP1/SNP2 locus complex Bound to the Xenobind Plates.

Oligonucleotides are synthesized, each representing one allele of the SNP2 (C/T) locus in the presence of Cy5-dCTP. The oligonucleotides represent the antisense sequence for each SNP2 allele as follows:

```
SNP2-(C detecting) oligo:
AGGGTGGT(G)CCAGAGGT            (SEQ ID NO:5)

SNP2-(T-detecting) oligo:
AGGGTGGT(A)CCAGAGGT            (SEQ ID NO:6)
```

Figure 2:
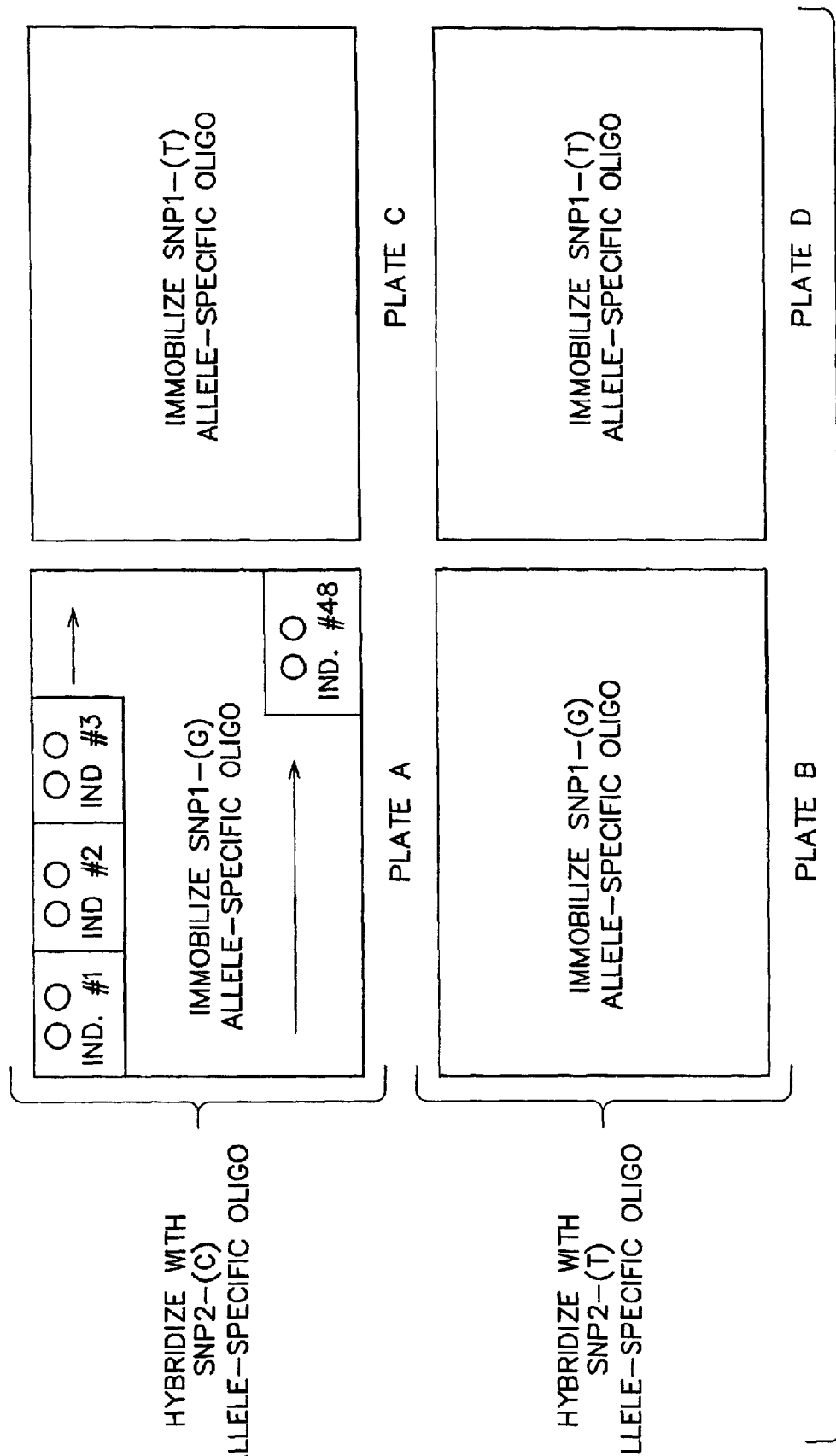
FIG. 2 is a diagram depicting an exemplary arrangement for performing hybridization reactions to determine haplotype.

As outlined in FIGS. 1 and 2, the SNP2-(C)-oligo and SNP2-(T)-oligo are each hybridized to one Xenobind plate bound with the SNP1 (G) oligo individual PCR products complex (FIG. 2, plates 2 & 4). Each SNP2 allele-specific oligonucleotide is diluted to 0.5 pmol/ml in TMAC hybridization solution+50×cold competitor. The hybridization protocol is identical to the protocol described in above (Step 4). Plates are read on a fluorescent microplate reader which can differentiate Cy3 and Cy5 signals. Cy5 signals are read to determine haplotype.

Phase II Hybridization Setup is shown in FIG. 2. Phase II hybridization setup is represented in Plates A–D. Plate A) SNP1 (G) allele-specific oligo is bound to the plate and Phase I-hybridized with 48 test genomes, each in duplicate wells. Plate A is then Phase II-hybridized with SNP2 (C) allele-specific oligo. Plate B) SNP1 (T) allele-specific oligo is bound to the plate and Phase I-hybridized with 48 test genomes, each in duplicate wells. Plate B is then Phase II-hybridized with SNP2 (C) allele-specific oligo. Plate C) SNP1 (G) allele-specific oligo is bound to the plate and Phase I-hybridized with 48 test genomes, each in duplicate wells. Plate C is then Phase II;-hybridized with SNP2 (T) allele-specific oligo. Plate D) SNP1 (T) allele-specific oligo is bound to the plate and Phase I-hybridized with 48 test genomes, each in duplicate wells. Plate D is then Phase 11-hybridized with SNP2 (T) allele-specific oligo.

Four haplotypes of the two SNP loci (SNP1=G/T and SNP2=C/T) are possible:

Haplotype I (G-C)

Haplotype II (G-T)

Haplotype III (T-C)

Haplotype IV (T-T)

Figure 3A:
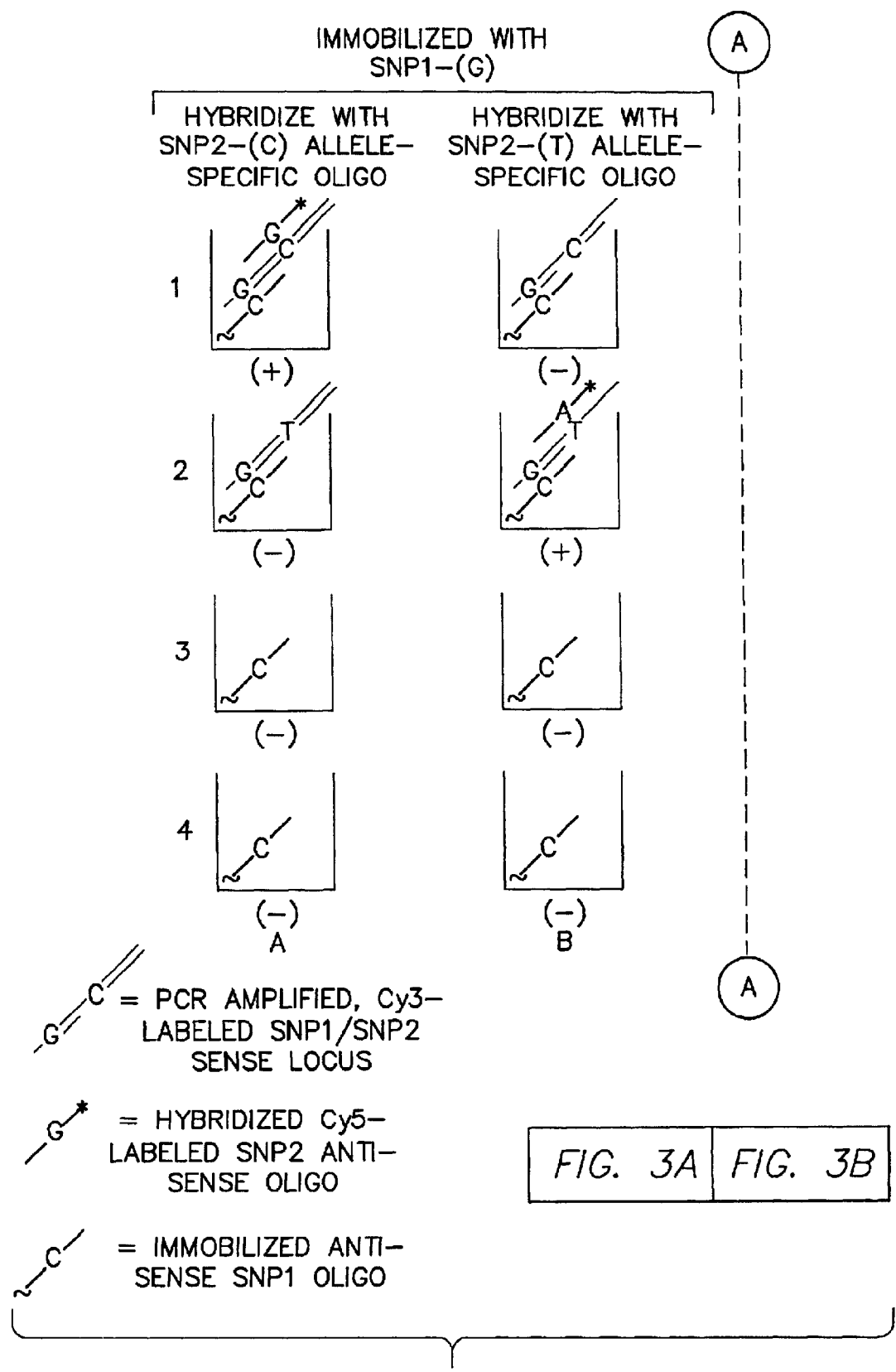
FIG. 3 is a diagram depicting each potential result resulting from a double hybridization method for a single chromosome at a polymorphic locus. There are four possible haplotypes, each individually depicted in one of the four rows. Columns A–D refer to the hybridization surfaces schematically pictured in FIG. 2.
Figure 3B:
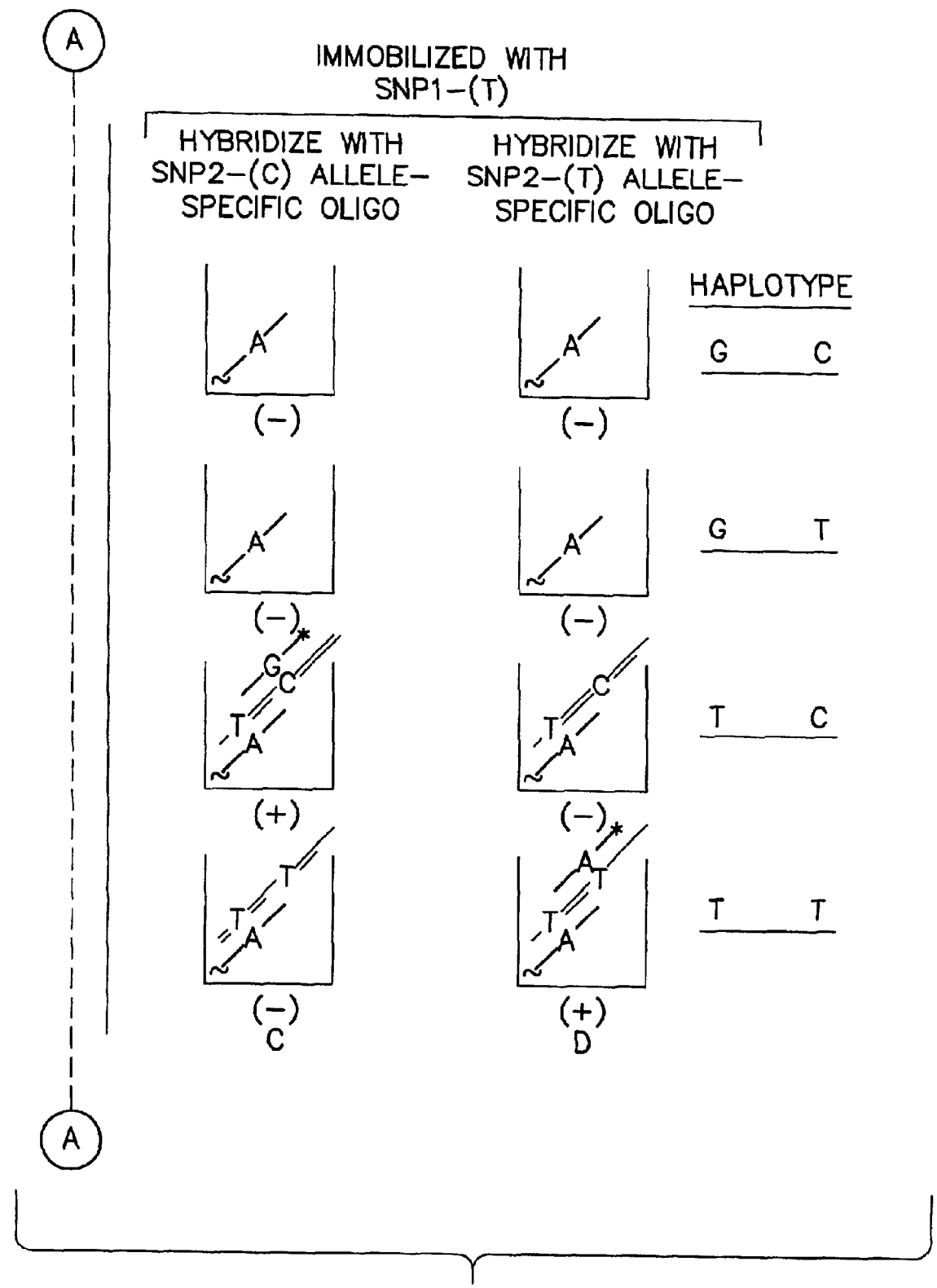

A schematic diagram depicting the determination of haplotype is shown in FIG. 3. In FIG. 3, the expected Phase II hybridization patterns are shown for the four possible haplotypes (rows 1–4) of the SNP1 (G/T) locus and the SNP2 (C/T) locus. Columns A–D refer to Plates A–D as outlined in FIG. 2. The (G-C) haplotype gives a positive signal on Plate A (well 1A). The (G-T) haplotype gives a positive signal on Plate B (well 2B). The (T-C) haplotype gives a signal on Plate C (well 3C). The (T/T) haplotype gives a signal on Plate D (well 4D).

SNP1 Genotype: If an individual possesses a G allele at the SNP1 locus, then that individual's PCR product will hybridize only to those wells containing the SNP1-(G)-detecting-oligo (FIG. 3, wells 1A, 1B, 2A and 2B). If this individual however, possesses a T allele at the SNP1 locus then hybridization will occur to those wells containing the SNP1-(T)-detecting-oligo (FIG. 3, wells 3C, 3D, 4C and 4D). Since the PCR products are Cy3 labeled, the genotype at SNP1 can be determined by detecting which wells have a Cy3 signal.

Haplotyping for One Chromosome

The haplotype for a particular chromosome is determined by hybridizing with either the SNP2-(C) or the SNP2-(T) allele-specific oligo. If an individual has a SNP1-SNP2 haplotype of G-C on one chromosome, then a Cy5 signal results when the SNP2 (C) specific oligo binds to a (G-C) PCR product/SNP1 (G) specific oligo complex bound to a well (FIG. 3, well 1A). If the individual, however, possesses a SNP1-SNP2 haplotype of G-T, then a Cy5 signal results when the SNP2 (T) specific oligo binds to a (G-T) PCR product/SNP1 (G) specific oligo complex (FIG. 3, well 2B).

Haplotype for Both Chromosomes

By examining the hybridization patterns, (i.e. which plates have wells with a Cy5 signal), the haplotype can be determined for both chromosomes. As outlined in FIG. 2: Plate A will detect SNP1 (G)/SNP2 (C); Plate B will detect SNP1 (G)/SNP2 (T); Plate C will detect SNP1 (T)/SNP2 (C) and Plate D will detect SNP1 (T)/SNP2 (T). Therefore, haplotypes can be scored for hybridization signals seen on each plate. They are as follows:

| Plate | SNP1-SNP2 | Haplotype |
| --- | --- | --- |
| A | G-C | I |
| B | G-T | II |
| C | T-C | III |
| D | T—T | IV |

Since each individual possesses two chromosomes, two haplotypes are expected to be detected per person. Since the maternal and paternal chromosome cannot be distinguished, ten haplotype combinations are possible. Their expected hybridization patterns are outlined in Table 1.

TABLE 1

Hybridization Patterns Expected For All 10 Possible Haplotype Combinations

| Haplotype | Plates Where Signal Is Detected For Each Individual |
| --- | --- |
| I, I | A |
| I, II | A, B |
| I, III | A, C |
| I, IV | A, D |
| II, II | B |
| II, III | B, C |
| II, IV | B, D |
| III, III | C |
| III, IV | C, D |
| IV, IV | D |

The ten possible haplotype combinations for both chromosomes are indicated in the left column of the chart. The plate (A–D) where the signal is expected to be detected for each haplotype combination, is indicated in the right column of the chart. It is expected that the haplotypes generated for the shuffled test samples will match the known haplotypes generated by sequencing.

Example 2

Haplotyping Procedure

Introduction

The following is the protocol used to detect genetic haplotypes consisting of two Single Nucleotide Polymorphisms (SNPs) in the human Beta-Adrenergic Receptor (BAR) gene. The assay was conducted in 96 well plate format, in which a set of four wells was used to detect each sample's haplotype. In order to distinguish the allele present for the first SNP detected, an amine labeled oligo was bound to the surface of the wells. One pair of wells contain an oligo, BAR-G, complimentary to a 17 base pair region including one allele of the SNP, while the remaining two wells contained an oligo, BAR-A, complimentary to a 17 base pair region including the other allele of the first SNP. This creates a situation where the Beta-Adrenergic Receptor gene probe binds preferentially to one set of wells over the other if only one allele of that SNP is present. If both alleles are present in the samples genome, the probe, produced using the Polymerase Chain Reaction (PCR), will bind to both sets of wells with proportionately equal success.

Following binding of the amine labeled oligo, the wells of the assay plate are washed to remove unbound oligo. The plate is then treated with blocking agents to prevent non-specific binding of the subsequent hybridization and detection components to the wells. Further washing removes the blocking agent and prepares the assay plate for hybridization.

In the hybridization, the sample of interest's BAR PCR product probe is introduced into each of the four wells used in the haplotype detection. In order to detect the genotype of the second SNP, a pair of biotin-labeled oligos, BAR-PIIG and BAR-PIIA, complimentary to the 17 base pair region including the two SNP alleles of the second SNP, are added as follows:

|  | Amine Oligo | Biotin Oligo | Positive Haplotype Detected |
|---|---|---|---|
| Well 1 | BAR-G | BAR-PIIG | G—G |
| Well 2 | BAR-G | BAR-PIIA | G-A |
| Well 3 | BAR-A | BAR-PIIG | A-G |
| Well 4 | BAR-A | BAR-PIIA | A—A |

Also added to the hybridization is either member of a pair of unlabeled cold competitor oligos. The cold competitor oligo DNA sequence is identical to the biotin-labeled oligo except does not contain a biotin label. The cold competitor oligo is added to the opposite wells as above and in some cases helps to enhance SNP discrimination. The addition of the cold competitor oligos is shown below.

|  | Cold Competitor Oligo |
|---|---|
| Well 1 | BARPIIAcc |
| Well 2 | BARPIIGcc |
| Well 3 | BARPIIAcc |
| Well 4 | BARPIIGcc |

Hybridization occurs by incubating the components together in the assay plate wells overnight. Probe that is non-complimentary to the amine oligo is washed from the wells, consequently removing any biotin oligo from the wells as well. Biotin oligo is also removed from wells in which the probe binds the amine oligo at the first SNP location but does not contain the allele of the second SNP that is complimentary to the SNP present in the biotin oligo sequence. Thus, biotin-labeled oligo remains after post-hybridization washing only in wells in which the probe is complimentary to the SNPs contained in the amine-labeled oligo and the biotin labeled oligo added to that well. This well will produce a positive signal for the haplotype it detects. Wells that do not meet this criterion will produce no signal, a "negative" signal.

The haplotypes present, of which there can be at most two of the four possible demonstrated haplotypes (one if the person has a homozygous haplotype), are detected by addition of a streptavidin-horseradish peroxidase conjugate to the assay plate. Biotin-streptavidin binding ensures that the peroxidase remains in the wells containing the positive haplotypes. Detection takes advantage of this with the addition of peroxidase substrates that form a chemiluminescent product in the positive wells and relatively none in the negative wells.

Haplotyping Protocol
Procedure
PCR Product Preparation for Use as Haplotyping Hybridization Probe
PCR Preparation
The PCR reactions were prepared as follows:
1. ABgene PCR Master Mix (Marsh Biomedical Products, Inc.,Rochester, N.Y., cat. #AB-0575)
Final conc. 1×

```
2. Forward primer
5'[P04]-ACTTGACAGCGAGTGTGCTG 3'      (SEQ ID NO:7)

3. Reverse primer
5'GTCCCTTTGCTGCGTGAC 3'              (SEQ ID NO:8)
```

Final primer concentration 0.1 µM for each primer
4. Genomic DNA template
Final conc. 1 ng/µl
Total reaction volume=50 µl The PCR reaction was conducted in PTC-225 DNA Engine Tetrad MJ Research (Waltham, Mass.)using the following PCR profile:
5 minutes at 94° C.
1 minute at 96° C.
1 minute at 56° C.
1:30 minutes at 72° C.
Repeat from step 2, 34times
10 minutes at 72° C.
4° C. constant hold The final product of this PCR reaction was an 1140 base pair fragment of the Beta-Adrenergic Receptor (BAR) gene sequence.

PCR Product Preparation Protocol
A. Purification of PCR Products

Each 50 µl PCR reaction was transferred to a MultiScreen-PCR Plate (Millipore, Bedford, Mass., cat. #MANU 030 50). The MultiScreen plate was placed on the vacuum manifold and the vacuum was engaged for ten minutes. Then 50 µl of $H_2O$ was added to each well of the multiScreen plate and the plate was shaken at 98 rpm at room temperature for five minutes. The DNA was eluted from the MultiScreen plate as described below in step B-3.

B. Exonuclease Digestion

Following the purification Lambda Exonuclease Digestion was preformed to produce single-stranded DNA. To do this: Gibco Lambda exonuclease, 6U/ul, (Life Technologies, Rockville, Md., cat. #28023–018) was added to 2×Lambda exonuclease buffer (10 mg/ml Glycine, 5mM $MgCl_2$ pH 9.4) at a rate of 1:50. Then 50 µl of the enzyme/buffer mix per well was dispensed from above to a Skirted Thermo-Fast 96 96 well PCR plate (Marsh cat. #AB-0800). The Millipore Multiscreen-PCR Plate purified PCR products were eluted and transferred to the PCR plate containing the 2×lambda exonuclease enzyme/buffer mixture. The PCR products were then digested for thirty minutes at 37° C. in PTC-225 DNA Engine Tetrad (MJ Research) and the reaction was heated 10 min. at 75° C. to stop the reaction.

C. Purification of Lambda Exonuclease Digested PCR Products

The 100 µl lambda exonuclease digest was transferred to a Millipore MultiScreen plate and purified as described above. Then the ssDNA was eluted in 50 µl $H_2O$ as described above.

D. Quantification of Purified Lambda Exonuclease Digested PCR Product 50 µl of the product from step C-3 above was placed into a COSTAR 96 well flatbottom UV plate (Corning, Inc., Acton, Mass., cat. #3635). Then the sample DNA concentrations were determined by reading the A260 of the samples in the TECAN Spectrafluor Plus (Durham, N.C.) compared to a standard curve of known ssDNA concentrations of equal volumes.

Haplotyping Hybridization Protocol
A. Bind Amine Labeled Oligo to Well of Assay Plate
Amine Labeled Oligo

```
BAR-G
5'NH2-(T)23CACCCAATGGAAGCCAT 3'     (SEQ ID NO:9)

BAR-A
5'NH2-(T)23CACCCAATAGAAGCCAT 3'     (SEQ ID NO:10)
```

150 pmol of amine labeled oligo was bound into the well of COSTAR DNA-BIND plate (Corning, Inc. cat. #2498) in oligo binding buffer (100 µl of Disodium phosphate, 50 mM, and EDTA, 1 mM, pH 8.5). Wells of the assay plate used for negative "no oligo" controls received 100 µl of binding buffer without amine-labeled oligo added. The oligo was allowed to bind by incubating for two hours at 37° C. while shaking at 98 rpm.

B. Removal of Unbound Oligo from the Assay Plate

Oligo binding buffer was removed by inverting the assay plate and dumping the contents of the wells into the sink. The plate was then gently shaken to remove any residual droplets of binding buffer. Any amine oligo was removed by washing the wells of the assay plate three times with 200 µl of 1×PBS wash buffer. Washes were added via a 12-channel pipettor and removed by the technique described above. One wash consisted of addition of the 200 µl wash buffer to the dry assay plate and its removal. All subsequent washes were carried out in an identical manner.

C. Block Assay Plate to Prevent Nonspecific Binding

After removal of the third wash, the wells of the assay plate were blocked with 200 µl blocking buffer (Disodium phosphate, 50 mM, and EDTA, 1 mM, pH 8.5, 3% Bovine Serum Albumin, 0.05% Tween 20). The plate was allowed to block by incubation for 1 hour at 37° C. while shaking at 98 rpm.

D. Prehybridization Wash

The plate was washed three times with 1×PBS, 200 ul per wash, as described above. Then the plate was washed once with 200 µl of TMAC-B solution (3M Tetramethyl-ammonium Chloride (Sigma-Aldrich Inc. St. Louis, Mo., product #T 3411), 50 mM Tris pH 8.0, 0.1% SDS, 1 mM EDTA) and the wash was allowed to incubate for 7 minutes at room temperature.

E. Hybridization Solution Addition

Hybridization solution was prepared in 96 well PCR plate using the following procedure.

Contents 0.4 pmol single-stranded BAR gene DNA probe 100.0 pmol cold competitor to bind opposite allele of SNP2 on BAR PCR product

```
BARPIIGcc   5' AGGAAATCGGCAGCTGT 3'   (SEQ ID NO:11)

BARPIIAcc   5' AGGAAATCAGCAGCTGT 3'   (SEQ ID NO:12)
```

3. 100.0 pmol biotinylated SNP2 detection oligo

```
BAR-PIIG
5' [Bio]-AGGAAATCGGCAGCTGT 3'    (SEQ ID NO:13)

BAR-PIIA
5' [Bio]-AGGAAATCAGCAGCTGT 3'    (SEQ ID NO:14)
```

4. The final volume was brought up to 100 µl such that hybridization occurs in TMAC-B solution as described above.

The Hybridization Solution was heated for 7 minutes at 95° C. in a PTC-100 Peltier Thermal Cycler from MJ research. Then 100 µl of hybridization solution was transferred to COSTAR DNA-BIND plate and hybridized overnight at 52° C. with shaking at 98 rpm.

F. Post-Hybridization Washes

The plate was washed three times with TMAC-B solution at room temperature with incubation in the third wash for 5 minutes at room temperature with shaking at 98 rpm. The plate was then washed once with TMAC-B solution at 52° C., with the wash incubated for five minutes at 52° C., with shaking at 98 rpm. The plate was then washed twice with 2×SSC followed by one wash with oligo binding buffer.

G. Perform Detection

100 µl of blocking buffer containing 1:500 Peroxidase-labeled Streptavidin (Kirkegaard and Perry Laboratories, cat. #474-3000) was added to each well of the assay plate. The plate was incubated 30 minutes at 37° C. with shaking at 98 rpm.

H. Remove Unbound Detection Molecules

The assay plate was washed three times with 1×PBS +0.05% Tween 20 wash buffer followed by washing twice with 1×PBS wash buffer.

I. Detect Haplotype

100 µl of 1:1 SuperSignal ELISA Femto Luminol/Enhancer Solution and SuperSignal ELISA Femto Stable Peroxide Solution (Pierce Chemical Company, Rockford, Ill., product #37075) was added and the assay plate shaken 1 minute at 98 rpm at room temperature. The assay plate chemiluminescence was then read using Tecan Spectrafluor Plus in chemiluminescence mode, with the gain set to 130.

Results

Figure 5:
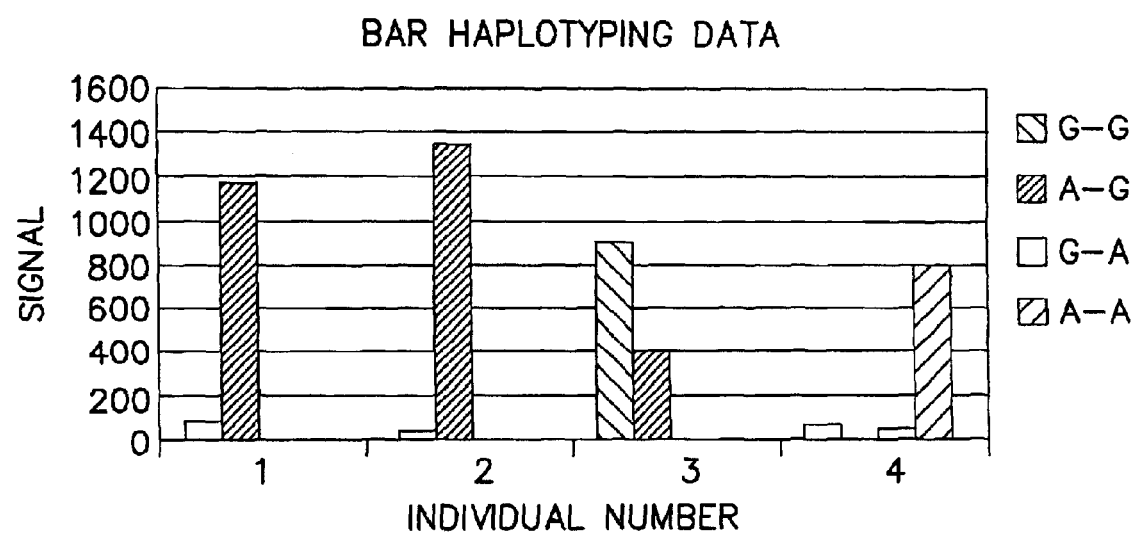
FIG. 5 is a graph depicting data generated from the haplotyping of 4 individuals (column sets 1–4). Haplotypes for each individual are as follows: #1-homozygote A-G, #2-homozygote A-G, #3-heterozygote G-G, A-G, #4-homozygote A-A.

The graph in FIG. 5 represents data generated from the haplotyping of 4 individuals. The signal generated from a negative control well (no PCR product added) was subtracted from the signal generated for each of the four wells analyzed for each individual. The background-subtracted signal was plotted for each well. From this analysis, the determined haplotypes for each individual are as follows: #1-homozygote A-G, #2-homozygote A-G, #3-heterozygote G-G, A-G, #4-homozygote A-A. Sequence analysis of several subcloned BAR products for each individual have confirmed these haplotypes. The data was normalized for hybridization differences between A and G of SNP #2.

Example 3

Haplotyping Assay Using Asymmetric PCR Products

Introduction

The hybridization described in Example 2 can also be performed in two steps. The PCR product and an appropriate cold competitor are added to wells containing bound amine-labeled oligo. These components are allowed to hybridize, then washed thoroughly to remove nonspecific binding. The second set of hybridization components are then added to the wells and allowed to hybridize. In this protocol, detection was carried out using a Streptavidin-alkaline phosphatase conjugate. Fluorescent products were then formed upon the addition of alkaline phosphatase substrates.

An alternate method of preparing the PCR product probe utilizes a method known as asymmetric PCR. In this method, the strand of interest is produced at a much higher frequency than its compliment during the PCR reaction. This is accomplished by increasing the concentration of the primer that initiates replication of the desired strand relative to the concentration of the primer producing the strand's compliment. This results in a large number of copies of the strand of interest being produced that have no compliment with which to bind. These single-stranded DNA fragments are readily available to take place in the hybridization that follows. Therefore, digestion of the opposite strand via exonuclease is not necessary when the PCR product is produced with asymmetric primer concentrations.

The locus of interest in this procedure can be found using accession #G54849 to search the Website of the National Center for Biotechnology Information's (NCBI) Genbank Database.

Procedure

A. Hybridization Components

| Well # | Haplotype Detected | Amine oligo bound |
|---|---|---|
| 1. | G-T | 4035AmG |
| 2. | G-C | 4035AmG |
| 3. | C-T | 4035AmC |
| 4. | C—C | 4035AmC |

Phase I Components (An equal amount of an asymmetric PCR reaction was added to each well in this hybridization)

| Well | Cold Competitor |
|---|---|
| 1. | 4035ColdCompG |
| 2. | 4035ColdCompG |
| 3. | 4035ColdCompC |
| 4. | 4035ColdCompC |

Phase II Components

| Well | Cold Competitor | Biotinylated SNP Detection Oligo |
|---|---|---|
| 1. | 4035Ccc | 4035-TB |
| 2. | 4035Tcc | 4035-CB |
| 3. | 4035Ccc | 4035-TB |
| 4. | 4035Tcc | 4035-CB |

Protocol for Haplotyping with Asymmetric PCR Product

PCR Preparation

PCR reactions were performed as follows:

1. ABgene PCR Master Mix (Marsh Biomedical Products, Inc., cat. #AB-0575) Final conc. 1×

```
2. Forward primer
(5' GAACAGCAATGCACATTACCATGG 3')     (SEQ ID NO:15)
Final primer concentration 0.2 µM 3. Reverse primer
(5' CTGTCAAGTATTTCTCCGCAGCATA 3')    (SEQ ID NO:16)
Final primer concentration 1.0 µM
```

4. Genomic DNA template Final conc. 1 ng/µl

Total reaction volume=50 µl

The PCR reaction was conducted in PTC-225 DNA Engine Tetrad (MJ Research) using the following PCR profile:

5 minutes at 94° C.

1 minute at 94° C.

1 minute at 56° C.

1 minute at 72° C.

Repeat from step 2, 34times 10 minutes at 72° C.

4° C. constant hold

The final product of this PCR reaction was a 289 base pair fragment of the human genome described above. This fragment contains SNPS at base pairs 35 (G/C) and 234 (C/T) of the PCR product. These two SNPs were the focus of this study.

Hybridization Protocol

A. Amine-labeled Oligo was bound to well of assay plate:

```
4035AmC
5' NH2-(T)23GCCACAATGAATGACAT    (SEQ ID NO:17)

4035AmG
or
5' NH2-(T)23GCCACAATCAATGACAT    (SEQ ID NO:18)
```

150 pmol of amine labeled oligo was bound into the well of COSTAR DNA-BIND assay plate (Corning, Inc. cat. #2498) in oligo binding buffer (100 µl of Disodium phosphate, 50 mM, and EDTA, 1 mM, pH 8.5). Wells of the assay plate used for negative "no oligo" controls receive 100 µl binding buffer without amine-labeled oligo added. The oligo was allowed to bind by incubating overnight at 4° C.

B. Removal of Unbound Oligo from Assay Plate

Oligo binding buffer was removed with a 12 channel vacuum apparatus. The remaining amine oligo was removed by washing the wells of the assay plate three times with 200 µl of 1×PBS wash buffer. Washes were added via a 12-channel pipettor and removed by the technique described above. One wash consists of addition of the 200 µl wash buffer to the dry assay plate and its removal. All subsequent washes are carried out in an identical manner.

C. Blocking Assay Plate to Prevent Nonspecific Binding

After removal of the third wash, the wells of the assay plate were blocked with 200 µl blocking buffer (Disodium phosphate, 50 mM, and EDTA, 1 mM, pH 8.5, 3% Bovine Serum Albumin). The plate was allowed to block by incubation for 1 hour at 37° C. with shaking at 98 rpm.

D. Prehybridization Wash

The wells were washed once with 1×PBS, 200µl per wash, as described above. The wells were then washed once with 200 µl of TMAC-B solution (3M Tetramethyl-ammonium Chloride (Sigma-Aldrich Inc. product #T3411), 50 mM Tris pH 8.0, 0.1% SDS, 1 mM EDTA). The final wash was allowed to incubate for 7 minutes at room temperature while treating the hybridization solution.

E. Perform Hybridizations

Phase I Hybridization

Hybridization solution was prepared in 96 well PCR plate using the following procedure:

Contents 1) 5–10 µl of 4035 locus asymmetric PCR DNA probe, with estimated concentration of 80 ng/µl.

2) 15 pmol cold competitor to inhibit binding of PCR product with SNP allele not being detected:

```
4035ColdCompG 5'ATGTCATTGATTGTGGC 3'  (SEQ ID NO:19)
or
4035ColdCompC 5'ATGTCATTCATTGTGGC 3'  (SEQ ID NO:20)
```

3) The final volume was then brought up to 100 µl such that hybridization occurs in TMAC-B solution as described above.

The Hybridization Solution was heated for 7 minutes at 95° C. Then 100 µl of hybridization solution was transferred to COSTAR DNA-BIND plate and allowed to hybridize overnight at 52° C. with shaking at 98 rpm.

Post-Hybridization Washes for Phase I Hybridization

Following the hybridization the plate was washed three times with TMAC-B solution at room temperature. The plate was then incubated 5 minutes at room temperature with shaking at 98 rpm. The plate was then washed once with TMAC-B solution at 52° C. with an incubation for five minutes at 52° C. with shaking at 98 rpm.

Phase II Hybridization
Contents
1) 45 pmol Biotinylated Phase II Detection oligo to bind $2^{nd}$ SNP:

```
4035-CB
5'Biotin-TGTATAATCAGAATTAT 3'   (SEQ ID NO:21)
or

4035-TB
5'Biotin-TGTATAATTAGAATTAT 3'   (SEQ ID NO:22)
```

2. 90 pmol Phase II cold competitor to inhibit binding of biotinylated oligo to $2^{nd}$ SNP loci containing allele not being detected:

```
4035-C 5'TGTATAATCAGAATTAT 3'   (SEQ ID NO:23)
or

4035-T 5'TGTATAATTAGAATTAT 3'   (SEQ ID NO:24)
```

3. The final volume is then brought up to 100 µl such that hybridization occurs in TMAC-B solution as described above.

100 µl of hybridization solution was transferred to COSTAR DNA-BIND plate and allowed to hybridize overnight at 52° C., with shaking at 98 rpm.

F. Post-Hybridization Washes for Phase II Hybridization

The plate was washed three times with TMAC-B solution at room temperature and then incubated 5 minutes at room temperature with shaking at 98 rpm. The plate was then washed once with TMAC-B solution at 52 C and incubate five minutes at 52° C. with shaking at 98rpm. Then the plate was wash twice with 2×SSC, with the washes carried out as described above. Then the plaste was washed once with oligo binding buffer.

Perform Detection

200 µl of 4 C 1×Elf Wash (ELF 97 mRNA In Situ Hybridization Kit, Component A. Molecular Probes, Eugene, Oreg., Cat. #E-6605) was added to the plate, the plate was incubated 5 minutes at room temperature, and the wash removed. 200 µl of Elf Blocking Buffer (ELF 97 mRNA In Situ Hybridization Kit, Component B) was then added, the plate incubated 45 minutes at room temperature, and the block removed. Then, 100 µl Elf Streptavidin Alkaline Phosphatase Conjugate (ELF 97 mRNA In Situ Hybridization Kit, Component J) diluted 1:50 in Elf Blocking Buffer, was added to the plate. The plate was incubated 30 minutes at room temperature with shaking at 98 rpm.

Following the incubation, the plate was washed the plate three times with 4 C 1×Elf Wash. Then 100 µl of ELF 97 phosphatase substrate working solution (ELF 97 mRNA In Situ Hybridization Kit, Component D 1:10, Component E 1:500, Component F 1:500, in Component C) was added to the plate and incubated 10 minutes in the dark. Following the incubation, the assay plate fluorescence (excitation 360 nm, emission 535 nm) was read.

After 45 minutes, the assay plate was washed once with 4 C 1×Elf Wash, and the wash was left in the plate. Then the assay plate fluorescence was read again as above.

Results

Sample Data

Figure 6:
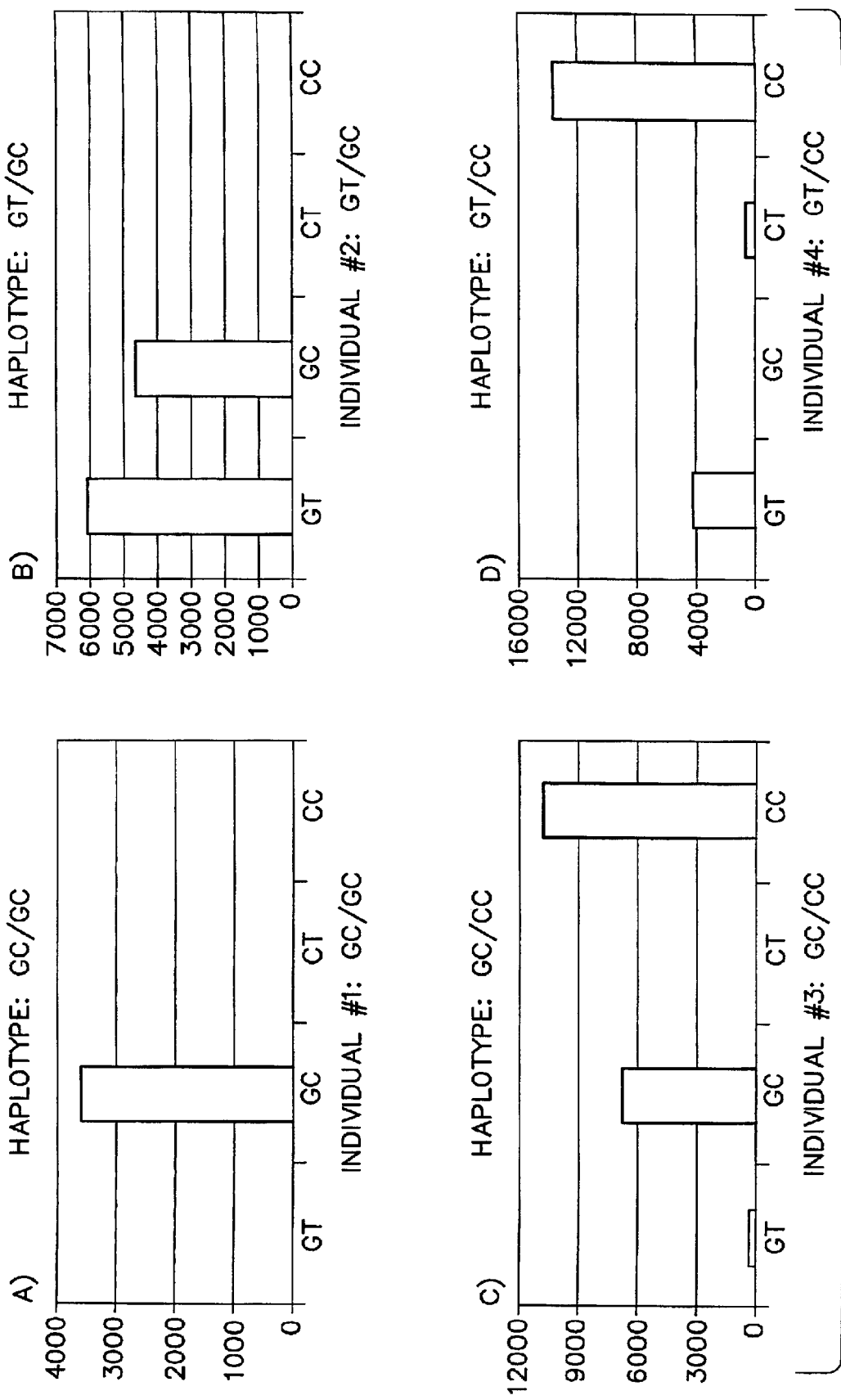
FIG. 6 is a diagram depicting four graphs that generated from the haplotyping of 4 individuals (graphs 1–4). Haplotypes for each individual are as follows: #1-homozygote G-C, #2--heterozygote G-T, G-C, #3-heterozygote G-C, C-C, #4--heterozygote G-T, C-C.

The four graphs in FIG. 6 represent data generated from the haplotyping of 4 individuals. The signal generated from a negative control well (no PCR product added) was subtracted from the signal generated for each of the four wells analyzed for each individual. The background-subtracted signal was plotted for each well. From this analysis, the determined haplotypes for each individual are as follows: #1-homozygote G-C, #2--heterozygote G-T, G-C, #3-heterozygote G-C, C-C, #4--heterozygote G-T, C-C. Sequence analysis of several subcloned products for each individual have confirmed these haplotypes.

The foregoing written specification is considered to be sufficient to enable one skilled in the art to practice the invention. The present invention is not limited in scope by the examples provided, since the examples are intended as illustrations of various aspects of the invention and other functionally equivalent embodiments are within the scope of the invention. Various modifications of the invention in addition to those shown and described herein will become apparent to those skilled in the art from the foregoing description and fall within the scope of the inventive claims. The advantages and objectives of the invention are not necessarily encompassed by each embodiment of the invention. All references, patents, and patent publications which are cited in this application are incorporated in their entirety here and by reference.

I claim:

1. A method for haplotyping, comprising:

analyzing a first polymorphic locus of a nucleic acid within a sample by specifically capturing the nucleic acid on a surface wherein the step of capturing the nucleic acid on the surface identifies only a first allele of a first SNP of the polymorphic locus, analyzing a second allele of the first SNP of the polymorphic locus by specifically capturing the nucleic acid on a surface wherein the step of capturing the nucleic acid on the surface identifies only the second allele of the first SNP of the polymorphic locus, wherein the nucleic acid is captured by hybridization with an ASO, separately analyzing a second SNP of a polymorphic locus of the captured nucleic acid by hybridization of the nucleic acids with labeled ASOs from solution to identify both alleles of the second SNP, and determining the haplotype based on the identification of each allele of each SNP.

2. The method of claim 1, wherein a first ASO complementary to a first allele of the first SNP and a second ASO complementary to a second allele of the first SNP are fixed to the surface and are used to capture the nucleic acid.

3. The method of claim 1, wherein the surface is a multiwell dish.

4. The method of claim 1, wherein the surface is a chip.

5. The method of claim 1, wherein the surface is a slide.

6. The method of claim 1, wherein the surface is a bead.

7. The method of claim 2, wherein each ASO corresponding to an allele of the first SNP further includes a spacer sequence.

8. The method of claim 7, wherein the spacer sequence is selected from the group consisting of a poly-T, poly-A, poly-C, and poly-G.

9. The method of claim 1, wherein each of the ASOs corresponding to an allele of the second SNP is hybridized independently to the nucleic acid sample.

10. The method of claim 1, wherein at least one of the ASOs complementary to an allele of the first SNP and at least one of the ASOs complementary to an allele of the second SNP contains a fluorescent label or quencher, the fluorescent label or quencher of the two ASOs, being distinct from one another.

11. The method of claim 1, wherein the alleles of the second SNP are analyzed simultaneously with one another.

12. The method of claim 1, wherein each of the ASOs complementary to an allele of the first SNP and each of the ASOs complementary to an allele of the second SNP contains a fluorescent label or quencher, the fluorescent label or quencher of each of the four ASOs, being distinct from one another.

13. The method of claim 1, wherein the nucleic acid sample is prepared by PCR amplification of a polymorphic locus from a genomic DNA sample.

14. The method of claim 1, wherein the nucleic acid sample is a reduced complexity genome.

15. The method of claim 1, wherein the nucleic acid sample is labeled with a first label.

16. The method of claim 1, wherein the presence of one set of alleles at the polymorphic locus is associated with a disease and the haplotyping method is performed to identify predisposition to the disease.

17. The method of claim 1, further comprising analyzing a third SNP of a polymorphic locus of the nucleic acid sample to identify both alleles of the third SNP, and determining the haplotype based on the identification of each allele of each SNP.

18. The method of claim 1, further comprising analyzing a fourth SNP of a polymorphic locus of the nucleic acid sample to identify both alleles of the fourth SNP, and determining the haplotype based on the identification of each allele of each SNP.

19. The method of claim 1, wherein the analysis of the first and second SNPs are performed simultaneously.

20. The method of claim 1, wherein the nucleic acid sample is an RNA genome.

21. The method of claim 20, wherein the RNA genome is made from cDNA.

22. The method of claim 1, wherein the nucleic acid sample is genomic DNA.

23. The method of claim 1, wherein the haplotype comprises an ordered combination of alleles in a defined genetic region that co-segregates.

* * * * *